United States Patent [19]

Kadow et al.

[11] Patent Number: 5,318,989
[45] Date of Patent: Jun. 7, 1994

[54] CYTOTOXIC BICYCLO [7.3.1.]TRIDEC-4-ENE-2,6-DIYNE COMPOUNDS AND PROCESS FOR THE PREPARATION THEREOF

[75] Inventors: John F. Kadow, Wallingford; Mark D. Wittman, Cheshire, both of Conn.

[73] Assignee: Bristol-Myers Squibb Company, New York, N.Y.

[21] Appl. No.: 993,184

[22] Filed: Dec. 18, 1992

Related U.S. Application Data

[60] Division of Ser. No. 782,942, Oct. 25, 1991, Pat. No. 5,198,560, which is a continuation-in-part of Ser. No. 621,503, Nov. 30, 1990, abandoned, which is a continuation-in-part of Ser. No. 515,387, Apr. 27, 1990, abandoned.

[51] Int. Cl.$^5$ .................. A61K 31/21; C07D 241/36; C07D 303/00
[52] U.S. Cl. .................. 514/511; 514/512; 514/513; 544/354; 544/355; 546/263; 546/265; 549/545; 549/553; 549/562; 558/260; 558/267; 558/276; 560/32; 560/115; 560/162; 560/256
[58] Field of Search .......... 558/260, 267, 276; 544/354, 355; 546/263, 265; 549/545, 553, 562; 560/32, 115, 162, 256; 514/511, 512, 513

[56] References Cited

PUBLICATIONS

Haseltine et al., J. Am. Chem. Soc., vol. 113, No. 10, pp. 3850–3866 (1991).
J. Am. Chem. Soc., 1987, 109:3461 and 3462.
J. Am. Chem. Soc., 1987, 109:3464 and 3466.
Kende, et al., Tet. Lett. 1988, 29:4217–4220.
Magnus, et al., J. Am. Chem. Soc., 1988, 110:1626–1628.
Magnus, et al., J. Am. Chem. Soc., 1988, 110:6921–6923.
Tomioka, et al., Tet. Lett., 1989, 30:851–854.
Magnus, et al., Tet. Lett., 1989, 30:3637–3640.
Danishefsky, et al., J. Am. Chem. Soc., 1988, 110:6890–6891.
J. Org. Chem., 1989, 54:2781–2783.
J. Am. Chem. Soc., 1989, 111:7638–7641.
Magnus, et al., J. Org. Chem., 1990, 55(6):1709–1711.
Danishefsky, et al., J. Am. Chem. Soc., 1990, 112:3253–3255.
Magnus, et al., Tetrahedron Letters, 1989, 30(15):1905–1906.

Primary Examiner—José G. Dees
Assistant Examiner—Porfirio Nazario
Attorney, Agent, or Firm—Prabodh I. Almaula

[57] ABSTRACT

The present invention relates to a novel and efficient process for the preparation of 8-hydroxybicyclo[7.3.1]-tridec-4-ene-2,6-diyne ring system which is part of the aglycone of esperemicin and to novel cytotoxic antitumor agents having said bicyclic ring system. The present invention also provides a method for treating mammalian malignant tumors by administering to an animal in need of such treatment an antitumor effective amount of a compound of the present invention.

29 Claims, No Drawings

CYTOTOXIC BICYCLO [7.3.1.]TRIDEC-4-ENE-2,6-DIYNE COMPOUNDS AND PROCESS FOR THE PREPARATION THEREOF

CROSS REFERENCE TO RELATED APPLICATION

This application is a division of our co-pending application Ser. No. 07/782,942 filed Oct. 25, 1991, now U.S. Pat. No. 5,148,560 which is a continuation-in-part of Ser. No. 07/621,503, filed Nov. 30, 1990, now abandoned, which is a continuation-in-part of Ser. No. 07/515,387, filed Apr. 27, 1990 now abandoned.

BACKGROUND OF THE INVENTION

1. Field of the Invention

The present invention relates to cytotoxic compounds, their use as antitumor agents, a novel process for their preparation, and intermediates produced thereby.

2. Background Art

Esperamicins and calichemicins belong to a class of extremely potent antitumor antibiotics isolated from microbial sources. Structure elucidation studies of the esperamicins and calichemicins were reported in *J. Am. Chem. Soc.*, 1987, 109:3461-3462, and *J. Am. Chem. Soc.*, 1987, 109:3464-3466, respectively. These antibiotics share a common aglycone core which contains a bicyclo[7.3.1]tridecane ring system with an allylic trisulfide side chain.

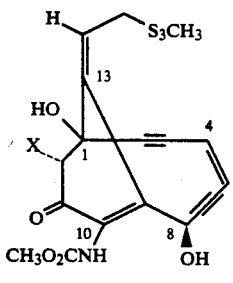

calichemicin aglycone: X = H
esperamicin aglycone: X = OH

The proposed mechanism of action of these antibiotics involves, first, a bioreductive activation of the trisulfide to generate a thiol which adds intramolecularly to the $\alpha,\beta$-unsaturated enone. The resulting change of hybridization of the bridgehead carbon atom brings the two ends of the diynene portion into closer proximity to coalesce and form a benzene 1,4-diradical which is capable of abstracting a hydrogen atom from the sugar phosphate backbone of DNA to effect single and double stranded breakage.

The unique structure and mechanism of action of these compounds have engendered much interest in the synthesis of the bicyclic diynene core fragment. A number of strategies have been devised to achieve ring closure of a cyclohexyl compound bearing the requisite diynene fragment to form the 10-membered ring.

Kende, et al., (*Tet. Lett.*, 1988, 29:4217-4220) treated 3,3-(1,2-ethylenedioxy)-5-(3-hexene-1,5-diynyl)-1-cyclohexenecarboxaldehyde with lithium bis(trimethylsilyl)amide, followed by removal of the ethylenedioxy ketone protecting group to provide 8-hydroxy-bicyclo[7.3.1]tridec-4,9-diene.-2,6-diyn-11one.

Magnus, et al., (*J. Am. Chem. Soc.*, 1988, 110:1626-1628) reported the preparation of 1-(TBSoxy)bicyclo[7.3.1]tridec-4-ene-2,6-diyn-10-one, dicobalt hexacarbonyl complex [TBS=t-butyldimethylsilyl] from 1,4-bis(TBSoxy)-4-(7-methoxy-3-heptene-1,5-diynyl)cyclohexene dicobalt hexacarbonyl complex upon treatment with titanium tetrachloride/diazabicyclo[2.2.2]octane (DABCO) at −78° C. Decomplexation of the product, however, caused the molecule to collapse into the corresponding benzenoid compound.

Magnus, et al., (*J. Am. Chem. Soc.*, 1988, 110:6921-6923) and Tomioka, et al., (*Tet. Lett.*, 1989 30:851-854) reported the preparation of 1-(TBSoxy)-bicyclo[7.3.1]tridec-4-ene-2,6-diyn-13-one (bicyclic ketone) from 1,6-bis-(TBSoxy)-6-(7-methoxy-heptene-1,5-diynyl)cyclohexene dicobalt hexacarbonyl complex upon treatment with titanium tetrachloride/DABCO, followed by decomplexation with iodine or trimethylamine oxide. Magnus, et al., further treated the bicyclic ketone product with potassium hexamethyldisilazane (KHMDS) and phenylselenium chloride to form the $\alpha$-phenylselenide which, upon oxidation with hydrogen peroxide, provided 1-(TBSoxy)-bicyclo[7.3.1]tridec-4,9-diene-2,6-diyn-13one (bicyclic enone). This latter product was also obtained as a minor product when the TBS enol ether of the bicyclic ketone was oxidized with selenium dioxide (Magnus, et al., *Tet. Lett.*, 1989, 30:3637-3640).

Danishefsky, et al., (*J. Am. Chem. Soc.*, 1988, 10:6890-6891) reported the preparation of 1-(TBSoxy)-8-hydroxy-11-methoxy-bicyclo[7.3.1]tridec-4,9,11-triene-2,6-diyne 13-spiroethylene epoxide from 3-methoxy-5-(TBSoxy)-5-(3-hexene-1,5-diynyl)-1,6-cyclohexadienecarboxaldehyde 6-spiro ethylene epoxide upon treatment with base. The product was further elaborated to provide inter alia 1,8-dihydroxybicyclo[7.3.1]tridec-4,9-diene-2,6-diyn-11,13-dione and the corresponding 11-ethylene ketal, and 1,8-dihydroxy-bicyclo[7.3.1]tridec-4-ene-2,6-diyn-11,13-dione. This latter compound was shown to cleave DNA in vitro (*J. Org. Chem.*, 1989, 54:2781-2783 and *J. Am. Chem. Soc.*, 1989, 111:7638-7641).

Magnus, et al., (*J. Org. Chem.*, 1990, 55(6):1709-1711) reported the preparation of 8-hydroxy-1-TBSoxybicyclo[7.3.1]tridec-4-ene-2,6-diyn-13-one by treating 6-TBSoxy-6-(7-oxo-3-hexene-1,5-diynyl)cyclohexanone dicobalt complex with dibutylboron triflate/DABCO to effect ring closure, followed by N-methyl-morpholine oxide to remove the cobalt carbonyl group.

Danishefsky, et al., (*J. Am. Chem. Soc.*, 1990, 112:3253-3255) reported the total synthesis of dl-calicheamicinone.

The known methods for ring closure either require the use of cumbersome precursors which are difficult to prepare, or they yield bicyclic diynenes lacking certain key functionalities. The process of the present invention circumvents these problems and provides a highly efficient route to bicyclic diynenes with multiple key functionalities. Furthermore, the present process results in the formation of a single pair of diastereomers and allows the introduction of the 8-hydroxy group having the same relative stereochemical configuration as the 8-hydroxy group of the esperamicin aglycone.

SUMMARY OF THE INVENTION

The present invention provides, in one aspect, a process for closing a 10-membered ring to form an 8-hydroxy-bicyclo[7.3.1]tridec-4-ene-2,6-diyne-13-one ring system. The process comprises the steps of: 1) reacting a dicobalt hexacarbonyl complexed 6-protected hydroxy 6-(7-oxo-3-heptene-1,5-diynyl)-2-cyclohexenone derivative with a nucleophilic species (Nu) capable of 1,4-conjugated addition to the enone; and 2) treating the resultant reaction product with a titanium reagent to effect ring closure to form the corresponding dicobalt hexacarbonyl complexed 1-protected hydroxy 10-Nu-B-hydroxy-bicyclo[7.3.1]tridec-4-ene-2,6-diyne-13-one derivative. The decomplexation of the compound obtained by this process is also part of the present invention.

Another aspect of the present invention provides a process for preparing an 8-hydroxy-bicyclo[7.3.1]tridec-4,9-diene-2,6-diyne-13-one compound which comprises oxidative elimination of the 10-Nu substituent of 10-Nu-8-hydroxy-bicyclo[7.3.1]tridec-4-ene-2,6-diyne-13-one.

Another aspect of the present invention provides 10-Nu-8-hydroxy-bicyclo[7.3.1]tridec-4-ene-2,6-diyne-13-one derivatives and their cobalt complexes, and 1-protected hydroxy-8-hydroxy-bicyclo[7.3.1]trideca-4,9-diene-2,6-diyne-13-one.

Also provided by the present invention are antitumor bicyclo[7.3.1]tridec-4-ene-2,6-diyne-13-one derivatives of formula VIIa.

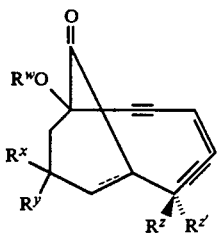

VIIa wherein ≡≡≡ is a double bond, single bond, or an epoxy; one of $R^x$ or $R^y$ is hydrogen and the other is hydrogen or hydroxy; or $R^x$ and $R^y$ together is an oxo group; $R^w$ is hydrogen, —C(O)R², —C(O)NR'R" or —C(O)OR'; $R^z$ and $R^{z'}$ are each hydrogen, or one of $R^z$ or $R^{z'}$ is hydrogen, and the other is hydroxy, —OC(O)R^s, —OC(O)NR'R" or —OC(O)OR'; R^s is hydrogen, $C_{1-8}$alkyl, $C_{3-6}$cycloalkyl, $C_{6-10}$aryl, $C_{7-14}$aralkyl, pyridyl or quinoxalyl; $R^t$ and $R^u$ are independently hydrogen, $C_{1-8}$alkyl, amino-substituted $C_{2-8}$alkyl, $C_{3-6}$cycloalkyl, $C_{6-10}$aryl, $C_{7-14}$aralkyl, pyridyl or quinoxalyl; $R^v$ is $C_{1-8}$alkyl, halo-substituted $C_{1-8}$alkyl, $C_{3-6}$cycloalkyl, $C_{6-10}$aryl or $C_{7-14}$aralkyl; or a pharmaceutically acceptable salt thereof.

DETAILED DESCRIPTION OF THE INVENTION

The numbering of the bicyclo[7.3.19 tridec-4-ene2,6-diyne ring system referred to in the specification is as follows:

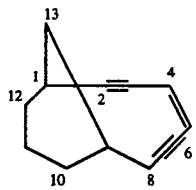

"10-Membered ring" is the ring defined by carbon atoms 1–9 and 13 of the bicyclo[3.7.1]tridec-4-ene-2,6-diyne ring system.

Dicobalt hexacarbonyl complexed carbon-carbon triple bond is represented by

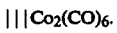

This group is also referred to in the specification as "cobalt carbonyl complex" or "cobalt complex". The dicobalt hexacarbonyl group may be used as carboncarbon triple bond protecting group. Cobalt complexed acetylene is the subject of the review by Nicholas, K. M., *Accounts in Chemical Research*, 1987, 20:207–214.

"TBS" is used throughout the specification as an abbreviation for t-butyldimethylsilyl [also referred to as (1,1-dimethylethyl)dimethylsilyl]. "Alkyl" includes straight and branched carbon chains. "Halo" or "halogen" includes fluorine, chlorine, bromine, and iodine. "Pharmaceutically acceptable salt" includes, where the compound contains one or more basic nitrogen atom, acid addition salts formed with inorganic acids such as hydrochloric acid, sulfuric acid, phosphoric acid, nitric acid, and the like, or with organic acids, such as acetic acid, citric acid, fumaric acid, lactic acid, tartaric acid, and the like.

The present invention provides a process for closing a 10-membered ring to form an 8-hydroxybicyclo[7.3.1]tridec-4-ene-2,6-diyne-13-one derivative of formula III which comprises the steps of: 1) reacting a dicobalt hexacarbonyl complexed 6-protected hydroxy 6-(7-oxo-3-heptene-1,5-diynyl)-2-cyclohexenone of formula I with a nucleophilic species (Nu) capable of 1,4-conjugated addition to the enone; and 2) treating the resultant reaction product with a titanium reagent to provide the corresponding dicobalt hexacarbonyl complexed 1-protected hydroxy 10-Nu-8-hydroxy-bicyclo[7.3.1]tridec-4-ene-2,6-diyne-13-one of formula III. The nucleophilic species is generally an organometallic reagent Nu-M wherein Nu is a nucleophilie capable of 1,4-conjugated addition to an α,β-unsaturated carbonyl compound, and M is a monovalent metal cation or a substituted metal having valency higher than one. This process is illustrated in Scheme I in which preferred reagents are exemplified. It will be appreciated that although preferred reagents are used to illustrate the invention in the following Schemes, the invention is by no means limited thereto.

Scheme I

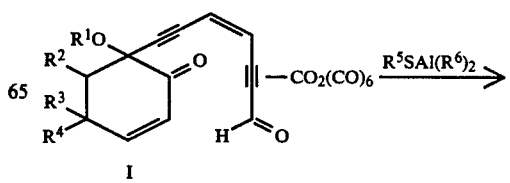

I

-continued
Scheme I

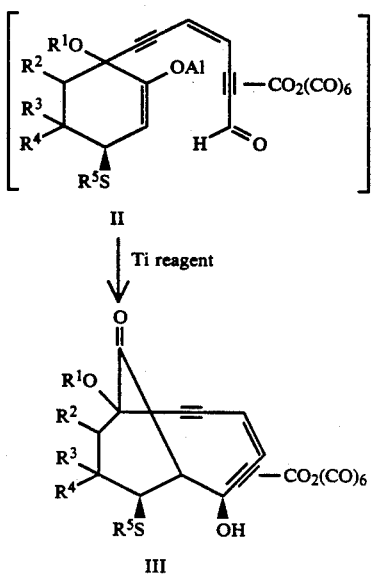

In Scheme I, $R^1$ is a hydroxy protecting group; $R^2$ is hydrogen or a protected hydroxy group; $R^3$ and $R^4$ are independently hydrogen or protected hydroxy group; or $R^3$ and $R^4$ taken together with the carbon atom to which they are attached represent a protected keto group. $R^5SAl(R^6)_2$ exemplifies Nu-M; $R^5$ and $R^6$ are independently $C_{1-5}$ alkyl, $C_{3-6}$ cycloalkyl, $C_{6-10}$ aryl, or $C_{6-10}$ aryl substituted with one or more groups selected from $C_{1-5}$ alkyl and $C_{1-5}$ alkoxy.

The choice of hydroxy protecting group and ketone protecting groups is not particularly limited; the protecting groups may be any that can be readily replaced with hydrogen under conditions which do not affect other functional groups in the molecule.

Examples of hydroxy protecting group include, but are not limited to, a) formation of ether linkage with i) lower alkyl or lower alkenyl group, e.g., methyl, ethyl, propyl, isopropyl, butyl, t-butyl, pentyl, and propenyl; ii) aralkyl group, e.g., benzyl, diphenylmethyl, triphenylmethyl, and tris(p-methoxyphenyl)methyl; and iii) triorganosilyl group, e.g., trimethylsilyl, t-butyldimethylsilyl, t-butyldiphenylsilyl, triisopropylsilyl; b) formation of acetal or ketal with, for example, tetrahydropyran, methoxymethyl, methoxyethoxymethyl, methylthiomethyl, tetrahydrothiofuranyl, and tetrahydrothiopyranyl; and c) formation of ester with i) optionally substituted lower alkanoyl, e.g., formyl, acetyl, propionyl, butyryl, trifluoroacetyl, chloroacetyl, methoxyacetyl, and phenoxyacetyl; ii) benzoyl or p-nitrobenzoyl; and iii) optionally substituted alkoxycarbonyl, e.g., methoxycarbonyl, ethoxycarbonyl, t-butyloxycarbonyl, isobutyloxycarbonyl, trichloroethoxycarbonyl, and tribromoethoxycarbonyl. Preferred hydroxy protecting group is t-butyldimethylsilyl.

A ketone protecting group may be one in which the oxo functionality has been converted into a ketal group. Examples of suitable ketal groups include, but are not limited to, a) dialkyl ketals such as dimethyl and diethyl ketals, and 2,2,2-trichloroethyl ketal; b) cyclic ketals such as 1,3-dioxolan, 1,3-dioxan, 2,2-dimethyl-1,3-dioxan, and 4-bromomethyl-1,3-dioxolan; c) thio ketals and hemithioketals such as 1,3-oxathiolan, 1,3-oxathian, 1,3-dithian, 1,3-dithiolan, and 2,2-di(lower alkyl)-1,3-dithian. Preferred ketone protecting groups are cyclic ketals such as 1,3-dioxolan and 1,3-dioxan.

In one preferred embodiment, $R^2$ is hydrogen. In another preferred embodiment, $R^3$ and $R^4$ are both hydrogen. Yet in another preferred embodiment, $R^1$ is a triorganosilyl group. In a more preferred embodiment, $R^2$, $R^3$ and $R^4$ are each hydrogen, and $R^1$ is a triorganosilyl group; most preferably, $R^1$ is t-butyldimethylsilyl.

According to Scheme I, a compound of formula I is treated with a thioaluminum compound having the formula $R^5S\text{-}Al(R^6)_2$, wherein $R^5$ and $R^6$ are organic residues such as $C_{1-5}$ alkyl, $C_{3-6}$ cycloalkyl, $C_{6-10}$ aryl, and $C_{6-10}$ aryl substituted with one or more groups selected from alkyl and alkoxy. Preferred thioaluminum compounds are dialkyl(phenylthio)aluminum, for example, dimethyl(phenylthio)aluminum, i.e., $(CH_3)_2AlSC_6H_5$. It will be understood that the thioaluminum reagent is an example of an organometallic compound, Nu-M as previously defined. In general, for Nu-M, the metal cation M may be one commonly used to stabilize an enolate, for example, an alkali metal, alkaline earth metal, aluminum, zinc, and the like; preferably, the metal cation is aluminum. The nucleophilic species Nu is one capable of 1,4-conjugated addition to an $\alpha,\beta$-unsaturated carbonyl compound, and which may be eliminated upon oxidation to regenerate a carbon-carbon double bond; examples of such nucleophilic species include sulfur and selenium nucleophiles; preferably, the nucleophilic species is a sulfur nucleophile.

The reaction is carried out in an inert aprotic organic solvent such as tetrahydrofuran, hexane, etc., or a mixture thereof, at temperature of below ambient temperature, suitably at 0° C. or below. The reaction generates in situ an aluminum enolate of formula II which may be directly subjected to the ring closure reaction described infra. The reaction mixture containing the aluminum enolate of formula II is treated with a titanium reagent to effect intramolecular ring closure to give novel cobalt complexed bicyclic diynene of formula III. Examples of suitable titanium reagents include, but are not limited to, titanium alkoxides $Ti[O\text{-}(C_{1-5})alkyl]_4$ and titanium alkoxide halides $XTi[O\text{-}(C_{1-5})alkyl]_3$ wherein X is halogen, such as bromine, chlorine, and iodine. Some specific examples of titanium reagents that may be mentioned are titanium isopropoxide Ti-$(OCH(CH_3)_2)_4$, titanium propoxide Ti-$(OCH_2CH_2CH_3)_4$, titanium ethoxide $Ti(OCH_2CH_3)_4$, and titanium isopropoxide chloride $Ti(OCH(CH_3)_2)_3Cl$. The nucleophile $R^5\text{-}S\text{-}Al(R^6)_2$ and the titanium reagent are used in at least equimolar amount, but preferably in excess, relative to the diynene. Thus up to about 10 equivalents of the sulfur nucleophile and up to about 80 equivalents of the titanium reagent may be employed. Preferably the sulfur nucleophile is used in a range of about 1.5 to 10 equivalents, and the titanium reagent in a range of about 1.5 to 80 equivalents, more preferably about 20 to 40 equivalents, relative to the diynene.

The cobalt carbonyl group of compounds of formula III may be removed to provide compounds of formula IV by treatment with known decomplexation agents such as iodine, iron (II) nitrate, and a tertiary amine N-oxide, e.g., N-methylmorpholine-N-oxide, trimethylamine-N-oxide, and the like. The preferred reagent is iodine. The reaction is carried out in an inert organic solvent such as benzene, dichloroethane, etc; a preferred solvent is benzene. The reaction temperature may be any that is conductive to product formation and may be ambient temperature. The decomplexation agent is used at least in equimolar amount relative to the diynene but, preferably, is used in excess of from about 1.5 to about 10 equivalents.

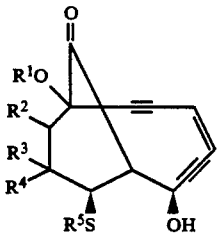

IV

The sulfide substituent at position 10 of the bicyclic diynene of formula IV may be oxidized to the corresponding sulfoide, the latter group is then eliminated to provide the enone product of formula Va. The dicobalt complexed bicyclic diynene of formua III may be similarly converted to the cobalt complexed enone of formula Vb.

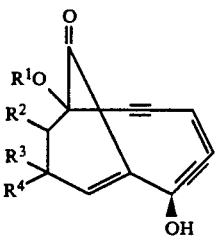

Va

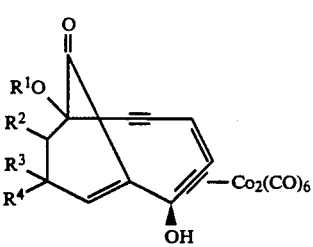

Vb

Methods of oxidation of sulfides and elimination of sulfoxides to provide α,β-unsaturated carbonyl compounds are generally well known in the art. The sulfice substituent of compounds of formulas IV and III may be oxidized to the corresponding sulfoide using a variety of reagents, including, but are not limited to, hydrogen peroxide, peracids, periodates, perborates, acyl nitriles, and the like. The reaction is carried out in a suitable inert organic solvent such as lower alcohol or aqueous lower alcohol at a temperature and for a period suitable to cause the elimination of the sulfoide to form the α,β-unsaturated bicyclic diynene products of formulas Va and Bv, respectively. Preferably, the reaction is carried out at room temperature, and the reaction is usually complete in less than 10 hours to yield the desired enone product. Compounds of formula Vb may be converted into compounds of formula Va by decompleation methods earlier described. It will be appreciated that, even though sulfide substituents are eemplified, selenide substitutents may be similarly converted to enones of formulas Va and Vb.

In one preferred embodiment of the invention, the sulfide substituent at position 10 of compounds of formulas IV and III is phenyl sulfide, and the oxidation/elimination reaction is carried out at room temperature with sodium periodate as the oxidizing agent, or with m-chloroperbenzoic acid (mCPBA) at about −78° C. with subsequent warming to a temperature sufficient to effect the elimination, e.g. ambient temperature.

Alternatively, a compound of formula III may be converted to the corresponding compound of formula Va in one step by treating the dicobalt hexacarbonyl complexed compound of formula III with metachloroperbenzoic acid (mCPBA). The reaction is carried out in an inert organic solvent such as methylene chloride at a temperature conducive to product formation, preferably at about room temperature. The reaction is generally complete in a few hours. mCPBA is used in at least equivalent amount to the bicyclic diynene compound, but preferably, it is used in excess of up to about 4 equivalents of the diynene.

In yet another method, a dicobalt hexacarbonyl complexed compound of formula III in inert organic solvent such as methylene chloride is treated with mCPBA at reduced temperature, e.g. at about −78° C.; optionally, an alkyne such as 1-hexyne is added to the reaction mixture, and the reaction mixture is then allowed to warm to ambient temperature. The resulting product is dissolved in acetone and treated with cerium ammonium nitrate (CAN) in the presence of a tertiary amine, e.g. triethylamine to provide the corresponding compound of formula Va. Preferably, CAN is used in excess relative to the diynene cobalt complex, more preferably at least 3 equivalents of CAN is used relative to the diynene.

The present invention also provides novel compounds of formulas III and IV which are useful as intermediates and are prepared by the processes described above. For compounds of formula IV the R¹ hydroxy protecting group may be removed using methods well known in the art to provide the corresponding 1-hydroxy compounds. The deprotection method used depends on the nature of the protecting group and may be, for example, hydrolysis under acidic or basic conditions, alcoholysis. When R¹ is t-butyldimethylsilyl, this group may be removed with, for example, trifluoromethanesulfonic acid tetrabutylammonium fluoride, or aqueous hydrofluoric acid in acetonitrile. In compounds of formula IV wherein R² is protected hydroxy, or wherein one of R³ or R⁴, or both are protected hydroxy, such hydroxy protecting group may also be removed by methods as described above for R¹. In compounds of formula IV wherein R³ and R⁴ together represent a protected ketone, deprotection may be effected by conventional methods such as acid hydrolysis.

Thus, another aspect of the invention provides a bicyclic diynene of formula VIa.

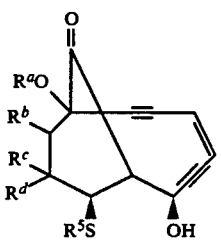

VIa wherein Rᵃ is hydrogen or a hydroxy protecting group; Rᵇ is hydrogen, hydroxy or a protected hydroxy group, $R^c$ and $R^d$ are independently hydrogen, hydroxy, a protected hydroxy group; or $R^c$ and $R^d$ together are an oxo group or a protected keto group; and $R^5$ is as defined above. A preferred embodiment provides compounds of formulas VIa wherein $R^a$ is hydrogen or a triorganosilyl group, preferably t-butyldimethylsilyl. Another preferred embodiment provides compounds of formulas VIa where $R^b$ is hydrogen Another preferred embodiment provides compounds of formulas VIa wherein $R^c$ and $R^d$ are each hydrogen Another preferred embodiment provides compounds of formulas VIa wherein $R_5$ is as previously defined, and is preferably a $C_{6\text{-}10}$aryl or substituted aryl group, and most preferably phenyl or alkoxy substituted phenyl. One particularly preferred embodiment provides compounds of formula VIa wherein $R^a$ is trialkylsilyl, preferably t-butyldimethylsilyl; $R^b$, $R^c$, and $R^d$ are hydrogen; and $R^5$ is phenyl, or alkyl or alkoxy substituted phenyl.

The present invention also provides novel compounds of formula VII wherein $R^1$ is a hydroxy protecting group; preferably $R^1$ is t-butyldimethylsilyl.

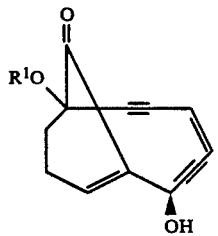

VII

In yet another aspect, the present invention provides novel compounds having the formula VIIa

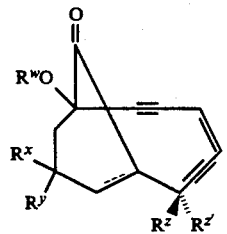

VIIa wherein ═ is a double bond, a single bond, or an epoxy; one of $R^x$ or $R^y$ is hydrogen and the other is hydrogen or hydroxy; or $R^x$ and $R^y$ together is an oxo group; $R^w$ is hydrogen, —C(O)$R^s$, —C(O)NR'$R^u$ or —C(O)O$R^v$; $R^z$, and $R^{z'}$ are each hydrogen, or one of $R^z$ or $R^{z'}$ is hydrogen, and the other is hydroxy, —OC(O)$R_s$, OC(O)NR'$R^u$ or —OC(O)O$R^v$; $R^s$ is hydrogen, $C_{1\text{-}8}$alkyl, $C_{3\text{-}6}$cycloalkyl, $C_{6\text{-}10}$aryl, $C_{7\text{-}14}$aralkyl, pyridyl or quinoxalyl; $R^t$ and $R^u$ are independently hydrogen, $C_{1\text{-}8}$alkyl, amino-substituted $C_{2\text{-}8}$alkyl, $C_{3\text{-}6}$cycloalkyl, $C_{6\text{-}10}$aryl, $C_{7\text{-}14}$aralkyl, pyridyl or quinoxalyl; $R^v$ is $C_{1\text{-}8}$alkyl, halo substituted $C_{1\text{-}8}$alkyl, $C_{3\text{-}6}$cycloalkyl, $C_{6\text{-}10}$aryl or $C_{7\text{-}14}$aralkyl; or a pharmaceutically acceptable salt thereof.

One preferred embodiment provides compounds of formula VIIb

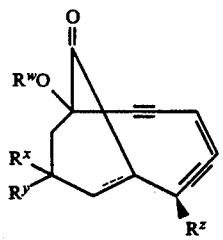

VIIb wherein ═ is a double bond, a single bond, or an epoxy; one of $R^x$ or $R^y$ is hydrogen and the other is hydrogen or hydroxy; or $R^x$ and $R^y$ together is an oxo group; $R^w$ is hydrogen, —C(O)$R^s$, —C(O)NR'$R^u$ or —C(O)O$R^v$; $R^z$ is hydrogen, hydroxy, —OC(O)$R^s$, —OC(O)NR'$R^u$ or —OC(O)O$R^v$; $R^s$ is hydrogen, $C_{1\text{-}8}$alkyl, $C_{3\text{-}6}$cycloalkyl, $C_{6\text{-}10}$aryl, $C_{7\text{-}14}$aralkyl, pyridyl or quinoxalyl; $R^t$ and $R^u$ are independently hydrogen, $C_{1\text{-}8}$alkyl, amino-substituted $C_{2\text{-}8}$alkyl, $C_{3\text{-}6}$cycloalkyl, $C_{6\text{-}10}$aryl, $C_{7\text{-}14}$aralkyl, pyridyl or quinoxalyl; $R^v$ is $C_{1\text{-}8}$alkyl, halo-substituted $C_{1\text{-}8}$alkyl, $C_{3\text{-}6}$cycloalkyl, $C_{6\text{-}10}$aryl or $C_{7\text{-}14}$aralkyl; or a pharmaceutically acceptable salt thereof. More preferably, $R^w$ is hydrogen.

Another preferred embodiment provides compounds of formula VIIb wherein ═ is a double bond or an epoxy, $R^w$, $R^x$ and $R^y$ are each hydrogen, $R^z$ is hydroxy, —OC(O)$R^s$, —OC(O)NR'$R^u$ or —OC(O)O$R^v$, $R^s$ is hydrogen, $C_{1\text{-}8}$alkyl, $C_{3\text{-}6}$cycloalkyl, $C_{6\text{-}10}$aryl, $C_{7\text{-}14}$aralkyl, pyridyl or quinoxalyl; $R^t$ and $R^u$ are independently hydrogen, $C_{1\text{-}8}$alkyl, amino-substituted $C_{2\text{-}8}$alkyl, $C_{3\text{-}6}$cycloalkyl, $C_{6\text{-}10}$aryl, $C_{7\text{-}14}$aralkyl, pyridyl or quinoxalyl; $R^v$ is $C_{1\text{-}8}$alkyl, halo-substituted $C_{2\text{-}8}$alkyl, $C_{3\text{-}6}$cycloalkyl, $C_{6\text{-}10}$aryl or $C_{7\text{-}14}$aralkyl. More preferably, $R^s$ is $C_{1\text{-}8}$alkyl or quinoxalyl; $R^t$ is hydrogen and $R^u$ is $C_{1\text{-}8}$alkyl, amino-substituted $C_{1\text{-}8}$alkyl, pyridyl or quinoxalyl; or $R^t$ and $R^u$ are each $C_{1\text{-}8}$alkyl; $R^v$ is $C_{1\text{-}8}$alkyl or halo-substituted $C_{1\text{-}8}$alkyl.

Another preferred embodiment provides compounds of formula VIIb wherein $R^w$ and $R^z$ are each hydrogen, ═ is a single bond or a double bond, one of $R^x$ or $R^u$ is hydrogen and the other is hydrogen or hydroxy, or $R^x$ and $R^y$ together is an oxo group. In a more preferred embodiment, $R^w$, $R^x$, $R^y$ and $R^z$, are each hydrogen, ═ is a single bond. In another preferred embodiment, $R^w$ and $R^z$ are each hydrogen, ═ is a double bond, one of $R^x$ or $R^y$ is hydrogen and the other is hydrogen or hydroxy, or $R^x$ and $R^y$ together is an oxo group.

Compounds of formula VIIb wherein $R^w$ is hydrogen; $R^z$ is hydroxy; one of $R^x$ or $R^y$ is hydrogen and the other is hydrogen or hydroxy; or $R^x$ and $R^y$ together is an oxo group; and ═ is a double bond may be obtained from corresponding compounds of formula Va in which $R^2$ is hydrogen upon removal of the various protecting groups using deprotecting methods known in formula IV. Compounds of formula VIIb wherein $R^w$, $R^x$ and $R^y$ are each hydrogen, $R^z$ is hydroxy, and ═ is a double bond, may be converted to the corresponding compound in which one of $R^x$ or $R^y$ is hydroxy, or $R^x$ and $R^y$ together is an oxo group using conventional allylic oxidation reagent such as selenium dioxide; preferably, in this process the hydroxy groups are protected with a suitable blocking group such as t-butyldimethylsilyl, prior to oxidation. The oxidation typically yields a mixture of the allylic alcohol and the corresponding oxo products; this mixture may be separated by conventional chromatography techniques. The protecting groups are removed after the oxidation and separation to provide the desired compounds.

The compound of formula VIIb wherein $R^w$, $R^x$, $R^y$ and $R^z$ are each hydrogen and $==$ is a single bond may be prepared by the procedure depicted in Scheme II.

such as a chlorinated hydrocarbon, e.g. methylene chloride, and typically at reduced temperature, for example, between $-78°$ C. and $0°$ C., for a period of time sufficient to effect cyclization of the starting material, generally the reaction is complete in one hour or less.

Scheme II

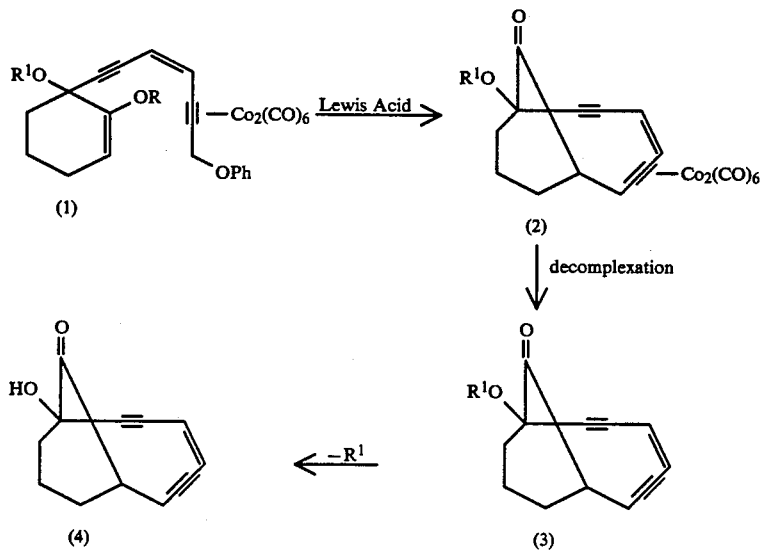

In Scheme II, $R^1$ and R are independently a hydroxy protecting group; $R^1$ is preferably t-butyldimethylsilyl, R is preferably trimethylsilyl. Compound (1) is depicted with the preferred leaving group, phenoxy; however, other leaving groups, for example, trifluoromethanesulfonyloxy, methoxy or acetoxy, may also be used. Cyclization of compound (1) to compound (2) is effected by treating compound (1) with a Lewis acid; suitable Lewis acids are for example titanium (IV) chloride, boron triflouride etherate, ethyl aluminum dichloride, titanium (IV) isopropoxide, and the like, or a mixture thereof; preferred Lewis acid include ethyl aluminum dichloride, and a mixture of titanium (IV) chloride and titanium (IV) isopropoxide. The Lewis acid is used in at least equimolar amount relative to compound (1). The reaction is carried out in a suitable inert organic solvent Dicobalt hexacarbonyl of compound (2) may be removed in a manner similar to that previously described for compounds of formula III using a decomplexation reagent such as ferric nitrate, trimethylamine N-oxide, mCPBA, or CAN. Preferably, the decomplexation agent is ferric nitrate, and the reaction is carried out in an alcohol solvent such as methanol or ethanol at room temperature to provide compound (3). The hydroxy protecting group of compound (3) is then removed using a conventional deprotecting method as previously discussed to provide compound (4).

Compound (3) can be converted to a compound of formula VIIb wherein $R^w$, $R^x$, $R^y$ and $R^z$ are each hydrogen and $==$ is a double bond by the following procedure depicted in Scheme III.

Scheme III

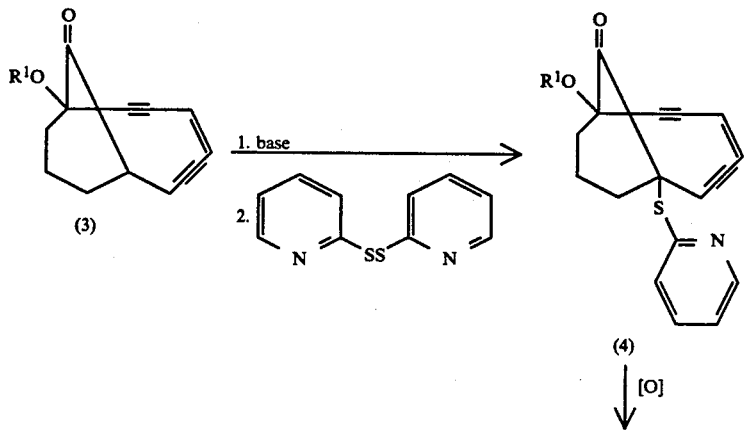

Scheme III

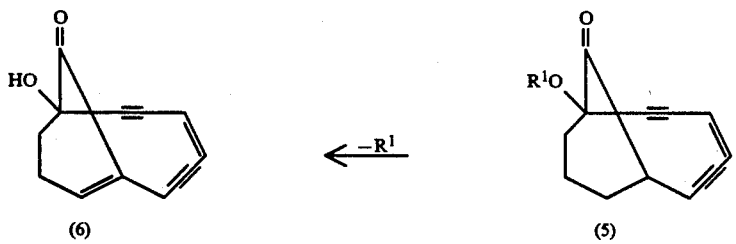

In Scheme III, R$^1$ is a hydroxy protecting group, preferably t-butyldimethylsilyl. Compound (3) is treated with a base to generate the enolate, which is reacted with 2,2'-dipyridyl disulfide to give the 9-pyridylthio-substituted intermediate, compound (4). In this step the base may be any capable of deprotonation, examples of which include potassium or lithium bis(trimethylsilyl)amide, lithium diisopropylamide, and the like; the preferred base is potassium bis(trimethylsilyl)amide. The reaction is carried out in an inert solvent such as tetrahydrofuran and at temperature below 0° C., e.g. at about −78° C. Compound (4) is oxidized to the corresponding sulfoxide using an oxidant such as mCPBA. The reaction is carried out in an inert organic solvent such as methylene chloride at a temperature, and for a period of sufficient time to cause the elimination of the sulfoxide to form compound (5); typically, at ambient temperature the elimination is substantially complete in about half an hour. Removal of the hydroxy protecting group on compound (5) provides compound (6). Although 2,2'-dipyridyl disulfide is illustrated as the preferred reagent, other substrates may be used to introduce a group functionally equivalent to the phenylthio group; such other suitable substrates are for example phenylselenyl chloride, aryldisulfides, and alkyl- or arysulfinyl chlorides.

Compound (5) may be converted to a compound of formula VIIb wherein R$^w$ and R$^z$ are each hydrogen, one of R$^x$ or R$^y$ is hydroxy, or R$^x$ and R$_y$ together is an oxo group. Thus compound (5) is treated with selenium dioxide or another agent suitable for allylic oxidation in a suitable inert organic solvent such as dioxane and at elevated temperature in the range of about 50° to 110° C. The product obtained typically containing a mixture of the starting material, the desired allylic alcohol as the major product (where R$^x$ or R$^y$ is hydroxy), and the desired dione (where R$^x$ and R$^y$ together form an oxo group); the desired components are separated by conventional chromatographic technique. The dione may also be prepared from the allylic alcohol using an ordinary oxidant such as manganese. The R$^1$ hydroxy protecting group is then removed to give the desired compounds.

The compound of formula VIIb wherein R$^w$, R$^x$ and R$^y$ are each hydrogen, R$^z$ is hydroxy, and ≡ is a single bond may be prepared by the procedure shown in Scheme IV.

Scheme IV

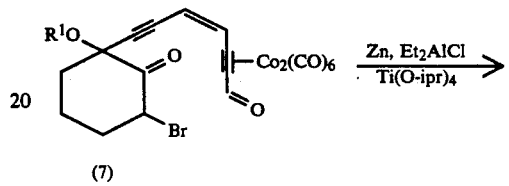

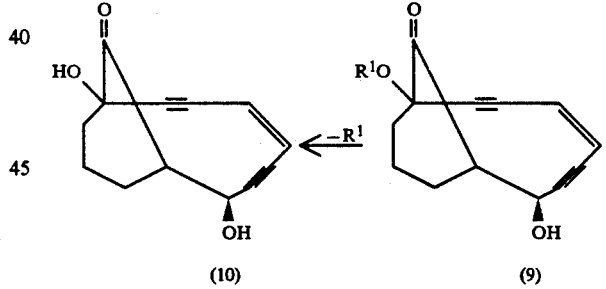

In Scheme IV, R$^1$ is a hydroxy protecting group, preferably t-butyldimethylsilyl. Compound (7) is treated with zinc, diethylaluminum chloride and titanium (IV) isopropoxide in tetrahydrofuran to effect ring closure to give compound (8). The cobalt carbonyl is removed using a decomplexation reagent as previously described, preferably the decomplexation agent is ferric nitrate, to give compound (9). Removal of the hydroxy protecting group yields the desired compound (10).

A compound of formula VIIa in which R$^z$ is hydrogen and R$^{z'}$ is hydroxy may be converted from its 8-epimer through the use of either of two common epimerization strategies known by practicing organic chemists. The preferred method, commonly known as the Mitsunobu inversion (reviewed in O. Mitsunobu, *Synthesis*, 1981, p. 1), entails reacting the hydroxy group with an aryl carboxylic acid such as benzoic acid or a substituted benzoic acid, e.g. p-nitrobenzoic acid, in the presence of triphenyl phosphine and a dialkylazodicarboxylate, e.g. diethyl or diisopropyl azodicarboxylate. The resulting aryl ester is subjected to ester hydrolysis or alcoholysis under acidic or mild basic condition to produce the desired epimerized alcohol.

In an alternate procedure, the hydroxy group is oxidized to a ketone using a reagent known to be useful in such transformations; for example, reagents based on activated DMSO (reviewed in Swern and Omura, *Tetrahedron.* 1978, 34:1651), the periodinanone reported in Dess and Martin, *J. Oro. Chem.*, 1983, 48:4155, other common oxidants such as barium manganate, pyridinium chlorochromate, pyridinium dichromate, manganese dioxide, or tetra-n-propyl ammonium perruthenate. The ketone thus formed may be selectively reduced with common reducing agents such as diisobutylaluminum hydride, sodium borohydride, other aluminum hydrides, or substituted borane reagents to provide the desired epimerized alchol. In this procedure, other functional groups that may also be oxidized or reduced by the reagents used are preferably first protected.

Compounds of formula VIIa wherein $R^w$ is an acyl group, or $R^z$ is an acyloxy group, or $R^w$ is acyl and $R^z$ is acyloxy, are prepared from the corresponding hydroxy compound by known acylation processes. The term or prefix "acyl" as used herein means generically or individually the groups —C(O)R$^s$, —C(O)NR$^t$R$^u$, and —C(O)OR$^v$. In general, where both —OR$^w$ and R$^z$ are hydroxy, the secondary hydroxy group, i.e. R$^z$, is preferably acylated over the tertiary hydroxy group, i.e. —OR$^w$. Thus, where acylation of only the tertiary hydroxy is desired, the secondary hydroxy is first protected with a conventional hydroxy protecting group, preferably, an organic silyl group such as the t-butyl-dimethylsilyl group which can be removed with e.g. aqueous hydrofluoric acid after the acylation of the tertiary hydroxy group. Where bisacylated products are desired, at least two equivalents of the the acylating agent is used relative to the bicyclic diynene.

A R$^s$C(O)— group may be introduced by employing the carboxylic acid R$^s$CO$_2$H or an acylating equivalent derived therefrom, examples of which include symmetrical or mixed acid anhydride, active esters, active amide, and acid halide. When the carboxylic acid is used, the reaction is preferably conducted in the presence of a condensing agent such as dicyclohexylcarbodiimide. Acid halide, for example acid chloride, is the preferred acylating agent and the acylation reaction is carried out generally at room temperature in an organic solvent, e.g. pyridine, methylene chloride, tetrahydrofuran, etc., and in the presence of an acid scavenger, e.g. a tertiary amine such as triethylamine, dimethylaminopyridine, etc.

A R$^t$R$^u$NC(O)— group may be introduced by converting the hydroxy group into a chloroformate using phosgene or trichloromethyl chloroformate; this intermediate is then reacted with an appropriate amine HNR$^t$R$^u$ either in the presence of a base, or an excess of the amine component may be used to neutralized the acid generated by the condensation. Where R$^t$ is hydrogen, the hydroxy group may be condensed with an isocyanate R$^u$N—C═O to give the carbamate. The reaction is carried out generally at a temperature of about 20° to about 100° C. in an organic solvent, e.g. pyridine, methylene chloride, tetrahydrofuran, benzene, toluene, etc, and optionally in the presence of a catalytic amount of dimethylaminopyridine.

A R$^v$OC(O)— group may be introduced by reacting the hydroxy group with a chloroformate R$^v$OC(O)Cl in an organic solvent, e.g. pyridine, methylene chloride, tetrahydrofuran, etc., at ambient temperature and in the presence of an acid scavenger such as a tertiary amine base, e.g. pyridine, triethylamine, dimethylaminopyridine, and the like.

Compound of VIIa wherein ═ is an epoxy may be prepared from the corresponding compound wherein ═ is a double bond by oxidation with hydrogen peroxide or a peracid. Prior to oxidation, it is desirable to protect any free hydroxy groups. The oxidation is preferably effected with hydrogen peroxide in the presence of sodium hydroxide. The reaction is carried out in an alcohol solvent such as methanol at ambient temperature. Any hydroxy protecting groups are then removed to give the desired epoxy product.

It will be appreciated that the various compounds produced by the novel process of the present invention can exist as optical isomers; the individual isomers, as well as racemic mixtures and diastereomeric mixtures, are all contemplated as being within the scope of the invention. Similarly, the novel process of the invention is applicable to the individual stereoisomers, as well as racemic and diastereomeric mixtures thereof. The stereochemical notations used in the structural formulas depicted in the specification and claims are meant to represent the relative orientations of the various substituents on the bicyclo[7.3.1]tridec-4-ene-2,6-diyne ring system and are not meant to restrict the compounds represented by these formulas to specific absolute configurations.

Preparation of Starting Materials

Turning now to the preparation of compounds of formula I which are the starting material used in the novel process of the invention. In the following Schemes, R$^1$, R$^2$, R$^3$ and R$^4$ have the same meanings as defined under formula I.

The cobalt complex diynene aldehyde of formula I may be prepared from the corresponding non-complexed acetal as depicted in Scheme V.

Scheme V

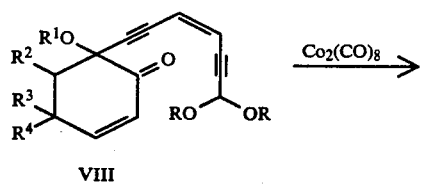

VIII

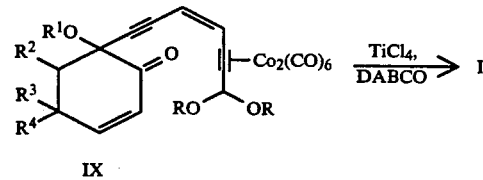

IX

Thus, the diynene acetal VIII is treated with dicobalt octacarbonyl at room temperature in an inert organic solvent such as heptane or methylene chloride. The cobalt complexed diynene acetal IX is converted into the corresponding aldehyde of formula I upon treatment with titanium tetrachloride and 1,4-diazabicyclo[2.2.2]octane (DABCO) at −65° C. in methylene chloride. In this Scheme, R is lower alkyl or the two R groups join to form a cyclic acetal. It is to be understood that the order of the two reaction steps depicted in Scheme V may be reversed; i.e., diynene acetal VIII may be first converted to the corresponding aldehyde by acid hydrolysis using, e.g., trifluoroacetic acid/chloroform, followed by complexation with dicobalt octacarbonyl to provide compound of formula I.

The diynene acetal VIII may be constructed from a 2-cyclohexenone derivative and a diynene acetal fragment. Several strategies may be employed to accomplish this end, and these are illustrated in Scheme VI.

Scheme VI

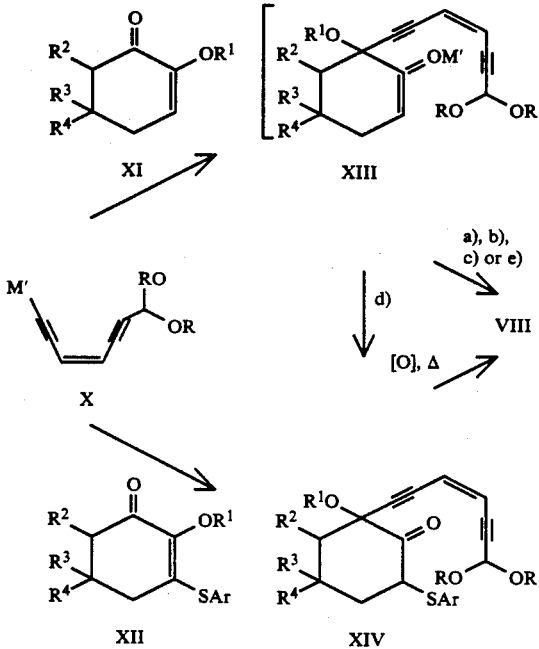

a: 1) H₂O; 2) t-butyldimethylsilyltriflate, triethylamine; 3) selenium dioxide
b: 1) t-butyldimethylsilyltriflate; 2) selenium dioxide
c: phenyl selenium chloride; 2) hydrogen peroxide
d: 1) ArSSO₂Ar
e: 1) H₂O; 2) LiHMDS; 3) allyl chloroformate; 4) cat. Pd(OAc)₂

In Scheme VI, M' is an alkali metal, for example, lithium, sodium, or potassium. R is a lower alkyl, or the two R groups joined to form a cyclic acetal. Ar is phenyl or phenyl substituted with a lower alkyl or alkoxy such as methyl, ethyl, methoxy, and ethoxy.

To elaborate on Scheme VI, the anion of the diynene acetal X is treated with a cyclohexenone of formula XI to generate a diynene-substituted cyclohexanone enolate of formula XIII. Or, the anion X is treated with 3-arylthio substituted 2-cyclohexenone of formula XII to yield a diynene-substituted cyclohexanone of formula XIV. Compounds of formulas XIII and XIV are further elaborated in order to obtain the desired cyclohexenone diynene acetal of formula VIII.

In one process of Scheme VI, the anion of the diynene acetal is treated with a 3-arylthio substituted 2-cyclohexenone XII at reduced temperature, e.g., at −78° C., followed by warming to room temperature. The resultant addition product XIV is then oxidized to sulfoxide using a conventional oxidizing agent, such as mCPBA or sodium periodate, and the reaction is preferably carried out with mCPBA at low temperature, e.g., −78° C. Heating the sulfoxide, e.g., refluxing in carbon tetrachloride or heating in pyridine at about 100° C.-110° C. generates the cyclohexenone diynene acetal of formula VIII. As a variation of this sequence, the sulfoxide of compound XII may be used in place of XII to yield the sulfoxide of compound XIV. The sulfoxide of XIV is then heated in an organic solvent, such as in refluxing heptyne or pyridine, and optionally in the presence of a reagent for trapping the sulfur elimination product, e.g., 2-mercaptobenzothiazole, to give compound of formula VIII.

In the second process of Scheme VI, the anion of the diynene acetal is treated with a cyclohexenone of formula XI in an inert solvent, such as tetrahydrofuran, initially at low temperature, e.g., from about −78° C. to about −50° C., then the reaction mixture is allowed to warm to ambient temperature to generate the metal enolate XIII which can be trapped and oxidized to the cyclohexenone diynene acetal of formula VIII. In one method, the metal enolate XIII is quenched with water at room temperature, and the resultant ketone is treated with t-butyldimethylsilyl trifluoromethanesulfonate (TBS triflate) and triethylamine at room temperature to provide the corresponding silyl enol ether. The silyl enol ether may also be obtained by treating the metal enolate XIII with TBS triflate at −78° C. The silyl enol ether is then oxidized using selenium dioxide at elevated temperature, e.g., refluxing temperature of the reaction mixture to provide the enone of formula VIII. Enone of formula VIII can also be prepared by treating the metal enolate XIII with phenylselenium chloride at −78° C., followed by oxidizing the resultant α-phenylselenide with hydrogen peroxide.

As depicted in Scheme VI, the metal enolate XIII may also be treated with ArSSO₂Ar to yield a compound of formula XIV which is converted into a compound of formula VIII as previously described. The enolate XIII may also react with dipyridyl disulfide to give the pyridylthio analog of XIV, which can also be similarly converted to VIII.

In yet another method for converting enolate XIII to enone of formula VIII, the ketone obtained from quenching XIII with water is treated with a base, e.g. LiHMDS and the enolate thus generated is reacted with ally chloroformate to provide the corresponding enol allyl carbonate. The reaction is carried out in an inert organic solvent such as tetrahydrofuran initially at low temperature, e.g. at about −78° C., and then the reaction is allowed to warm to a temperature tending to favor O-acylation over C-acylation, generally in the range of about −10° C. to about 25° C. The enol allyl carbonate is converted to compound of formula VIII with a catalytic amount of palladium diacetate refluxing in acetonitrile.

Compound of formula (I) may be prepared in an analogous manner by reacting the phenoxy (in place of the two —OR groups) analog of compound X with cyclohexenone XI in THF at about 0° C., and then trapping the enol with a silyl chloride, e.g. trimethylsilyl chloride to give the silyl enol ether. Treatment of the silyl enol ether with dicobalt octacarbonyl provides compound (I). The phenoxy diynene starting material may be prepared by the method provided infra for the synthesis of compound of formula (X) substituting 3,3-diethoxypropyne with phenoxypropyne.

Compound (7) may also be prepared analogously. Thus 2-TBSoxy-2-cyclohexenone is reacted with bromine in methylene chloride and in the presence of triethylamine to provide 3-bromo-2-TBSoxy-2-cyclohexenone. This compounds is treated with a diynene acetal of formula X, dicobalt octacarbonyl, and then titanium tetrachloride/DABCO under conditions given above to provide compound (7).

The diynene acetal X may be synthesized using the following procedure. Cis-1,2-dichloroethylene is reacted with 3,3-diethoxypropyne in the presence of copper iodide, palladium tetrakis(triphenylphosphine) and n-butylamine, at room temperature and in the absence of light. The product, (Z)-5-chloro-1,1-diethoxy-4-pentene-2-yne is treated with trimethylsilylacetylene in the presence of copper iodide, palladium tetrakis(triphenylphosphine), and n-butylamine at room temperature and away from light to provide (Z)-7,7-diethoxy-1-trimethylsilyl-3-hepten-1,5-diyne. The corresponding anion is then generated by treatment with an alkali metal hydroxide, such as lithium hydroxide.

Cyclohexenones of formulas XI and XII may be prepared from commercially available starting materials. For example, 2-TBSoxy-2-cyclohexenone (XI, $R^1$=TBS, $R^2$=$R^3$=$R^4$=H) may be obtained from 1,2-cyclohexandione upon treatment with a base, such as triethylamine, imidazole or lithium diisopropylamide (LDA), followed by TBS triflate or TBS chloride. 3-(4-Methylphenyl)-2-TBSoxy-2-cyclohexenone (XII, $R^1$=TBS, $R^2$=$R^3$=$R^4$H, Ar=4-methylphenyl) can be prepared from 1,2-cyclohexanedione upon treatment with a base such as lithium bis(timethylsilyl)amide, followed by 4-methylphenyl 4-methylbenezenethiosulfonate; the resulting product is treated with a base, e.g. triethylamine or imidazole, and TBS triflate or TBS chloride to yield the desired product.

Compounds of formula XI, wherein $R^3$ and $R^4$ are not both H, can be prepared from 1,4-cyclohexanedione. Thus, 1,4-cyclohexanedione is first converted into a mono-protected form (XVa) wherein $R^{3'}$,$R^{4'}$, together with the carbon atom they are attached, represent a protected ketone group.

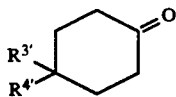

XVa

Preferably, the ketone is protected by conversion to a ketal. Monoketal of formula XV may be obtained upon treatment with a controlled amount of an alcohol, such as methanol, an orthoester, such as methyl orthoformate, a ketal, such as 2,2-dimethoxypropane, or a diol, such as ethylene glycol. Some 1,4-cyclohexanedione monoketals are available commercially, e.g., monoethylene ketal and mono-2,2-dimethyltrimethylene ketal.

Mono-protected 1,4-cyclohexanedione (XVa) may be converted to 4-protected hydroxy cyclohexanone by first reducing the ketone to a hydroxy group using, e.g., sodium borohydride. The hydroxy group may be protected using known methods and reagents, e.g., by treating with a base such as sodium hydride and benzyl bromide. The ketone protecting group is then removed to provide 4-protected hydroxy cyclohexanone

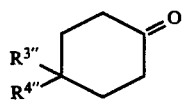

XVb wherein one of $R^{3''}$ and $R^{4''}$ is hydrogen and the other is a protected hydroxy.

Compounds of formulas XVa and XVb are further elaborated to provide compounds of formula XI, wherein $R^3$ and $R^4$ are not both H. One such reaction sequence is illustrated in Scheme VII.

Scheme VII

In Scheme VII, $R^3$ and $R^4$ are not both hydrogen but are otherwise as defined under formula I. Cyclohexanone XV, prepared according to procedures described above, is treated first with a base, such as lithium diisopropylamide (LDA), and then with benzenesulfonothioic acid, S-phenyl ester to generate the corresponding α-phenylsulfide compound XVI. A compound of formula XVI is oxidized with lead tetraacetate to provide α-acetoxy-α-phenylthiocyclohexanone derivative of formula XVII, which may be converted to a corresponding silyl enol ether of formula XVIII by first treating with a strong base, such as LDA, followed with a silylating agent $R^1$-L, wherein $R^1$ is a triorganosilyl group and L is a leaving group. $R^1$-L may be, for example, TBS triflate and iodotrimethylsilane. The silyl enol ether of formula XVIII is converted to the corresponding 2-silyloxy-2-cyclohexenone derivative of formula XIX upon base-catalyzed hydrolysis.

Cyclohexenones of formulas XI and XII in which $R^2$ is hydrogen may be converted into their corresponding α-hydroxy derivatives ($R^2$=OH) by treating the cyclohexenone with a base such as lithium bis(trimethylsilyl)amide, followed by an hydroxylating agent such as the reagent known as MoOPh (Aldrich). The α- hydroxy group may then be protected using conventional protecting groups to provide cyclohexenones of formulas XI and XII in which $R^2$ represents protected hydroxy.

Compounds of formula I may also be prepared from a 7-protected hydroxy-3-heptene-1,5-diyne and an arylsulfocyclohexenone as depicted in Scheme VIII,

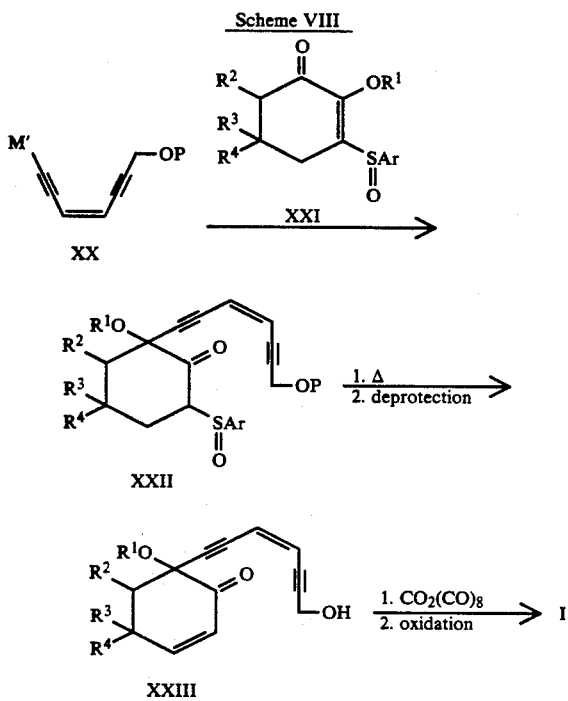

In Scheme VIII, M', $R^1$, $R^2$, $R^3$, $R^4$ and AR have the same meaning as previously defined; P is a hydroxy protecting group. The hydroxy protecting group is not particularly limited, the preferred one being tetrahydropyranyl group. Protected diynene alcohol XX may be prepared from cis-1,2-dichloroethylene and protected propargyl alcohol in a manner similar to that described supra for the preparation of the diynene acetal X. The arylsulfocyclohexenone XXI is obtained from the corresponding arylthiocyclohexenone XII upon oxidation with mCPBA.

The condensation of the protected diynene alcohol XX and the arylsulfocyclohexenone XXI is carried out in an inert organic solvent such as tetrahydrofuran at an initial temperature of $-78°$ C. The reaction temperature is allowed to gradually rise to ambient temperature and the reaction is generally completed in a few hours. The product XXII thus obtained is heated in pyridine at about 105° C. to cause the elimination of the aryl sulfoxide thus generating the corresponding enone. Deprotection of the hydroxyl group may be accomplished using conventional techniques known in the art; for example, the tetrahydropyranyl group may be removed by acid hydrolysis. The free alcohol of formula XXIII is then converted to the corresponding cobalt complexed diynene aldehyde of formula I by treatment with dicobalt octacarbonyl and oxidation with t-butoxy magnesium bromide and (azodicarbonyl)dipiperdine.

The present invention provides an efficient method for constructing an 8-hydroxylcyclo[7.3.1]tridec-4-ene-2,6-diyne-13-one ring system. The products that may be obtained by this process, e.g., compounds of formulas IV, Va and Vb may be further elaborated to provide the esperamicin/calichemicin aglycone. Thus, compounds of formulas IV, Va and Vb are useful intermediates in the synthesis of antitumor compounds belonging to the esperamicin/calichemicin structure class. In addition, compounds of formulas Va and Vb may be coupled to known antitumor agents, e.g., chlorambucil may be linked to the 8-hydroxy group using an acylating equivalent thereof, such as the acid chloride, to yield active hybrid molecules having more desirable biological activity profile than the parent compound.

Compounds of formula VIIa are cytotoxic compounds and are, therefore, useful in inhibiting unwanted rapid proliferation of cells, such as that in the neoplastic process. As therapeutic agents for treating mammalian tumors sensitive to a compound of formula VIIa, these compounds may be administered in the same manners as those suitable for esperamicin and calichemicin. Thus, they may be administered by systemic or topical routes; parenteral administration is the preferred route. The dosage may be similar to that used for esperamicin; but in general, because compounds of the present invention are less cytotoxic than esperamicin, dosage ten to one thousand times that for esperamicin may be tolerated and may be more suitable. The route of administration and the optimal dosage may be readily ascertained by those skilled in the art and will, of course, vary depending on factors such as the type and site of tumor to be treated, and individual patient charateristics, such as extent of the disease, age, weight, and the like.

The invention includes within its scope pharmaceutical compositions containing an effective tumor-inhibiting amount of a compound of formula VIIa in combination with an inert pharmaceutically acceptable carrier of diluent. Such compositions may be made up in any pharmaceutical form appropriate for the desired route of administration. Examples of such compositions include solid compositions for oral administration such as tablets, capsules, pills, powders and granules; liquid compositions for oral administration such as solutions, suspensions, syrups or elixirs; and preparations for parenteral administration such as sterile solutions, suspensions or emulsions. The pharmaceutical compositions may also be manufactured in the form of sterile solid compositions which can be dissolved in sterile water, physiological saline or some other sterile injectable medium immediately before use.

Furthermore, compounds of formula VIIa are effective in causing damages to DNA and in double stranded DNA cleavage. They are, therefore, valuable as laboratory reagents for such purposes.

Biolooical Activity

Compound of Example 4 was evaluated in vitro against three human colon tumor cell lines: HCT-116, HCT/VM46, and HCT/VP35; the latter two are resistant to teniposide and etoposide, respectively. The in vitro cytotoxicity assay involved growing tumor cells on microtitre plates employing established tissue culture methods. The concentration of the test compound required to inhibit cell growth by 50% ($IC_{50}$) was then determined by four-fold serial dilution technique. In the experiment, etoposide and teniposide were included as positive controls. The results obtained are shown in Table I:

TABLE I

Results of In Vitro Cytotoxicity Assay

| Compound | IC$_{50}$ (µg/ml) | | |
|---|---|---|---|
| | HCT-116 | HCT/VM46 | HCT/VP35 |
| Example 4 | 0.037 | <0.031 | 0.042 |
| | 0.043 | <0.031 | 0.046 |
| | <0.031 | 0.047 | 0.072 |
| Etoposide | 0.101 | 4.24 | 5.14 |
| | 0.128 | 3.57 | 6.29 |
| | 0.140 | 2.08 | 6.75 |
| Teniposide | 0.077 | 0.313 | 0.084 |
| | 0.088 | 0.237 | 0.091 |
| | 0.083 | 0.236 | 0.111 |

The compound of Example 4 was also evaluated against transplantable murine P388 leukemia. CDF$_1$ mice were implanted intraperitoneally with a tumor inoculum of 10$^6$ cells of P388 leukemia and treated with various doses of the test compound Six mice were used for each dose level and 10 mice were treated with saline to serve as control. The test compound was administered intraperitoneally on 5 consecutive days starting on day 1 after tumor implantation. Antitumor activity is expressed as % T/C which is the ratio of mean survival time (MST) for the drug-treated group to the MST of saline-treated control group.

A compound showing a % T/C of 125 or greater is considered to have significant antitumor activity. The results of P388 test on day 39 of the experiment for compound of Example 4 are provided in Table II. The data indicates this compound as having high activity against P388 leukemia.

TABLE II

In Vivo Activity Against P388 Leukemia

| Dose (mg/kg/dose) | Med. Survival Time (d) | % T/C | Survival d.5 (39)* |
|---|---|---|---|
| 32 | 7 | 64 | 6/6 |
| 16 | 9.5 | 86 | 6/6 |
| 8 | >39 | >355 | 6/6 (4) |
| 4 | 20.0 | 182 | 6/6 |
| 2 | 16.5 | 150 | 6/6 |
| 1 | 13 | 118 | 6/6 |
| Control | 11 | 100 | 10/10 |

*The number in parenthesis represents the number of surviving mice on day 39.

Compounds of Examples 6, 8 and 15 were evaluated against P388 leukemia using the same protocol given above. Compound of Example 6 showed a maximum %T/C of 235 at a dose of 20 mg/kg/dose (with one mouse surviving on day 31); compound of Example 8 showed a max. %T/C of 145 at a dose of 15 mg/kg/dose; and compound cf Example 15 showed a max. %T/C of 230 at a dose of 40 mg/kg/dose.

SPECIFIC EMBODIMENTS

Preparation of Starting Materials

The structures of the compounds described in this section are provided on separate pages following the Examples section.

Preparation I. (Z)-7,7-diethoxy-1-trimethylsilyl-3-hepten-1,5-diyne [compound A]

(a) (Z)-5-chloro-1,1-diethoxy-4-pentene-2-yne [compound B]

Neat cis-1,2-dichloroethylene (4.5 ml, 60 mmol) followed by butylamine (8.0 ml, 81 mmol) was added to a solution of copper iodide (0.90 g, 4.73 mmol) and palladium tetrakis(triphenylphosphine) (1 g, 0.86 mmol) in 40 mL of dry benzene stirring at 25° C. under argon. Immediately thereafter, a solution of 3,3-diethoxypropyne (5 g, 39 mmol) in 10 mL of benzene was added via cannula. The reaction vessel was wrapped in foil to shield it from light, and the reaction mixture was stirred for 4.2 h at 25° C. The dark brown reaction mixture was filtered by suction through a coarse frit and diluted to approximately 10 ml with diethylether. The solution was washed with 75 mL of water and 120 mL saturated brine, and the organic layer was dried over anhydrous Na$_2$SO$_4$ and then concentrated in vacuo. The residue was flash chromatographed on SiO$_2$ using 5%, then 10%, and then 15% diethylether/pentane as eluent to provide the desired product as a clear liquid (3.9 g, 55%).

$^1$H NMR (CDCl$_3$) δ: 6.46 (d, J=7.5 Hz, 1H), 5.92 (dd, J=1.5, 7.6 Hz, 1H), 5.45 (d, J=1.4 Hz, 1H), 3.80 (m, 2H), 3.64 (m, 2H), 1.26 (t, J=7.0 Hz, 3H).

(b)

(Z)-7,7-diethoxy-1-trimethylsilyl-3-heptene-1,2-diyne

A solution of 5-chloro-1,1-diethoxy-4-pentene-2-yne (compound B, 3.8 g, 20 mmol) in 10 mL of benzene was added via cannula to a solution of palladium tetrakis(-triphenyl-phosphine) (1.1 g, 0.95 mmol) and copper iodide (0.47 g, 2.46 mmol) in 20 mL benzene stirring at 25° C. under argon. Immediately thereafter, butylamine (4 mL, 40 mmol), followed by trimethylsilylacetylene (5 mL, 40 mmol) was added via syringe. The reaction vessel was wrapped in foil, and the reaction mixture was stirred at 25° C. for 4.25 h. The reaction mixture was poured into 100 mL water and 100 mL diethyl ether and extracted. The aqueous layer was reextracted with 2×40 mL of diethyl ether. The combined organic extracts were washed with 50 mL saturated aqueous NaCl, dried over Na$_2$SO$_4$, and concentrated in vacuo. Flash chromatography over SiO$_2$ using 2%, then 4%, and then 5% diethylether/pentane as eluent provided the title compound (2.7 g, 54%) as a light brown oil.

$^1$H NMR (CDCl$_3$) δ: 5.89 (s, 2H), 5.46 (s, 1H), 3.83-3.75 (m, 2H), 3.69-3.61 (m, 2H), 1.25 (t, J=7.1 Hz, H), 1.40E-4 (s, 9H).

$^{13}$C NMR (CDCl$_3$) δ: 130.6, 111.6, 92.8, 92.0, 79.4, 61.3, 15.2.

Preparation II.

(Z)-6-[[(1,1-dimethylethyl)dimethylsilyl]oxy]-6-(7,7-diethoxy-3-heptene-1,5-diynyl)-2-cyclohexenone [compound C]

(a)

(Z)-6-[[(1,1-dimethylethyl)dimethylsilyl]oxy]-6-(7,7-diethoxy-3-heptene-1,5-diynyl) cyclohexanone [compound D]

Solid lithium hydroxide monohydrate (3 g, 71.5 mmol) was added to a solution of (Z)-7,7-diethoxy-1-trimethylsilyl-3-heptene-1,5-diyne (compound A, 3.20 g, 12.6 mmol) in 30 mL of tetrahydrofuran and 5 mL water. The reaction mixture was stirred for 4 h and poured into 100 mL of pentane and 50 mL of H$_2$O. The organic layer was washed with 50 mL saturated aqueous NaCl, dried over Na$_2$SO$_4$, and then concentrated in vacuo by rotary evaporation. Methylene chloride (50 mL) was added, and the solution was again concentrated by rotary evaporation and then placed under high vaccuum for 25 min to provide approximately 3.3 g of a light brown oil which was immediately dissolved in 160 mL of dry tetrahydrofuran. The solution was cooled to −78° C., and then lithium hexamethyl-disilazane (1.0 M, in tetrahydrofuran, 15.5 mL, 15.5 mmol) was added via syringe in one portion. The reaction mixture was stirred for 20 min, and then a solution of 2-tertbutyldimethylsilyloxy-2-cyclohexenone (3.65 g, 6.12 mmol) in 10 mL of dry tetrahydrofuran, which had been precooled to approximately −50° C., was added in one portion via syringe. The reaction mixture was stirred for 1 min, and then all of the cooling baths were removed. The reaction mixture was allowed to stir for 2.5 h and attain ambient temperature (25° C.) to generate in situ the lithium enolate. The enolate was quenched with water to provide the corresponding ketone as follows. The reaction mixture was poured into 400 mL of 9:1 ethyl acetate/diethyl-ether and 100 mL of water. The mixture was extracted, and then the aqueous layer was reextracted with 100 ml of 1:1 ethyl acetate/diethyl ether. The combined organic extracts were washed with 50 mL saturated aqueous NaCl, dried over anhydrous $Na_2SO_4$, and concentrated in vacuo. Flash chromatography using 3%, then 4%, and then 5% ethyl acetate/hexane provided 3.50 g (72%) of the desired title cyclohexanone as a very faint green oil.

$^1$H NMR ($CDCl_3$) δ: 5.92 (s, 2H), 5.41 (s, 1H), 3.80–3.70 (m, 2H), 3.65–3.55 (m, 2H), 2.88 (dt, J=13.3, 5.7 Hz, 1H), 2.46 (td, J=7.7, 12.2 Hz, 1H), 2.27–2.23 (m, 1H), 2.00–1.58 (m, 5H), 1.24 (t, J=7.08 Hz, 6H), 0.91 (s, 9H), 0.046 (s, 3H), 0.018 (s, 3H).

(b)
(Z)-1,26-bis[[[(1,1-dimethylethyl)dimethyl]silyl]oxy]-6-(7,7-diethoxy-3-heptene-1,5diynyl]cyclohexene
[compound E]

Neat tert-butyldimethylysilyl trifluoromethanesulfonate (0.62 mL) was added via syringe to a solution of triethyl-amine (0.69 mL, 2.72 mmol) and compound D prepared above (0.54 g, 1.33 mmol) in 20 ml of methylene chloride stirring at 25° C. under a nitrogen atmosphere. The reaction mixture was stirred for 22.5 h and then poured into 100 mL of methylene chloride and 50 mL of water. The organic layer was dried over anhydrous $Na_2SO_4$ and concentrated in vacuo, and the residue was flash chromatographed on $SiO_2$ using 3% ethyl acetate/hexane to provide the title bis-silyloxy cyclohexene (683 mg, 98%) as a clear liquid.

IR (NaCl, Film): 3046, 2954, 2932, 2890, 2858, 2212, 1660, 1468, 1252 cm$^{-1}$.

$^1$H NMR ($CDCl_3$) δ: 5.88 (d, J=11.0 Hz, 1H), 5.81 (dd, J=11.0, 1.3 Hz, 1H), 4.82 (t, J=3.9 Hz, 1H), 3.79–3.74 (m, 2H), 3.64–3.58 (m, 2H), 2.05–1.99 (m, 4H), 1.81–1.56 (m, 2H), 1.24 (t, J=7.1 Hz, 6H), 0.94 (s, 9H), 0.87 (s, 9H), 0.21 (s, 3H), 0.18 (s, 3H), 0.17 (s, 3H), 0.16 (s, 3H).

$^{13}$C NMR ($CDCl_3$) δ: 151.1, 121.4, 118.1, 105.0, 102.1, 92.2, 91.5, 82.9, 81.5, 70.2, 61.2, 41.1, 26.1, 24.4, 18.8, 18.8, 18.4, 15.3, −2.8, −3.0, −4.3, −4.4.

(c)
(Z)-6-[[(1,1-dimethylethyl)dimethylsilyl]oxy]-6(7,7-diethoxy-3-heptene-1,5-diynyl]-2-cyclohexenone
[compound C]

Selenium dioxide (600 mg, 5.41 mmol) was added to a solution of oompound E (1.0 g, 1.98 mmol) in 60 mL of dioxane. The reaction mixture was refluxed for 1.5 h, an additional 300 mg (2.71 mmol) of selenium dioxide was added, and reflux continued for an additional 3 h. The reaction mixture was then poured into 150 mL of ethyl acetate and 100 mL of saturated aqueous NaHCO$_3$. The aqueous layer was reextracted with 50 mL of ethyl acetate. The combined organic layers were dried over anhydrous $Na_2SO_4$, concen-trated in vacuo, and purified by flash chromatography on $SiO_2$ using 3% and then 5% ethyl acetate/hexane to provide the title cyclohexenone (620 mg, 77%) as a clear oil.

Anal. calcd. for $C_{23}H_{34}O_4Si$: C, 68.62; H, 8.51.
Found: C, 68.26; H, 8.42.

$^1$H NMR ($CDCl_3$) δ: 6.93–6.88 (m, 1H), 5.98 (doublet of multiplets, J=9.49 Hz, 1H), 5.89 (s, 2H), 5.4I (s, 1H), 3.80–3.70 (m, 2H), 3.66–3.55 (m, 2H), 2.82–2.66 (m, 1H), 2.53–2.40 (m, 1H), 2.35–2.16 (m, 2H), 1.24 (t, J=7.04 Hz, 6H), 0.89 (s, 9H), 0.22 (s, 3H), 0.20 (s, 3H).

$^{13}$C NMR ($CDCl_3$) δ: 194.4, 150.7, 127.4, 120.5, 120.0, 95.4, 92.4, 92.2, 84.6, 82.5, 73.6, 61.3, 39.0, 26.0, 25.4, 18.5, 15.3, −3.0, −3.1.

Preparation III. Cobalt, hexacarbonyl
[μ-[6-[(5,6-η:5,6-η)
-7,7-diethoxy-3-heptene-1,5-diynyl]-6-[[(1,1-dimethylethyl) -dimethylsilyl]oxy]-2-cyclohexenone]],
di(Co-Co), (Z) [compound F]

Solid dicobalt octacarbonyl (0.542 g, 1.58 mmol) was added to a solution of compound C (0.64 g, 1.584 mmol) stirring at 25° C. under a nitrogen atmosphere in 28 mL of anhydrous heptane. The reaction mixture was stirred for h and concentrated in vacuo. Flash chromatography using 2%, then 3%, and then 5% ethyl acetate/hexane on $SiO_2$ provided 728 mg (66%) of the desired title cobalt complex as a dark purple oil.

Anal. calcd. for $C_{29}H_{34}O_{10}SiCo_2$:
C, 50.59; H, 4.98; N, 0.0.
Found: C, 50.56; H, 4.99; N, 0.0.

IR (NaCl, Film): 2978, 2956, 2932, 2896, 2858, 2094, 2056, 2028, 1700, 1624, 840 cm$^{-1}$.

$^1$H NMR ($CDCl_3$) δ: 6.89 and 6.86 (t, 3.91 Hz, 0.5H), 6.78 (d, J=11.1 Hz, 1H), 5.99 and 5.96 (t, J=2.0 Hz, 0.5H), 5.87 (d, J=11.1 Hz, 1H), 5.58 (s, 1H), 3.83–3.75 (m, 2H), 3.68–3.59 (m, 2H), 2.50–2.43 (m, 2H), 2.26 (t, 5.6 Hz, 2H) 1.21 (t, J=6.9 Hz, 6H), 0.84 (s, 9H), 0.17 (s, 3H), 0.07 (s, 3H).

$^{13}$C NMR ($CDCl_3$) δ: 199.1 (b), 192.6, 149.9, 137.1, 26.9, 110.5, 101.6, 98.9, 96.0, 85.3, 82.0, 73.6, 63.2, 8.2, 25.7, 24.2, 18.3, 15.0, −3.3, −3.5.

Preparation IV. Cobalt, hexacarbonyl
[μ-[6-(5,6-η:5,6-η)
-7-oxo-3-heptene-1,5-diynyl]-6-[1,1-dimethylethyl)-dimethylsiyl]oxy]-2-cyclohexenone]] di-(Co-Co), (Z)
[compound G]

Titanium tetrachloride (0.195 mL, 1.79 mmol) was added via syringe to a solution of the cobalt complexed cyclohexenone compound F (0.41 g, 0.60 mmol) and 1,4-diazabicyclo[2.2.2]octane (67 mg, 0.60 mmol) in 40 mL of methylene chloride stirring at −65° C. under a nitrogen atmosphere. The reaction mixture was stirred for 5 min and then poured into 60 mL of methylene chloride and 25 mL of water. The mixture was extracted, and then the aqueous layer was reextracted with 10 mL methylene chloride. The combined organic layers were dried over $Na_2SO_4$, filtered, concentrated by rotary evaporation, and chromatographed to provide the title cobalt complexed aldehyde (301 mg, 82%) as a thick viscous reddish purple semi solid.

Anal. calcd. for $C_{25}H_{24}O_9SiCo_2$:
C, 48.87; H, 3.94; N, 0.00.
Found: C, 48.42; H, 3.82; N, 0.04

¹H NMR (CDCl₃) δ: 10.39 (s, 1H), 6.93 (dt, J=10.1, 4.0 Hz, 1H), 6.82 (d, J=10.6 Hz, 1H), 6.03 (dt, 10.1 1.9 Hz, 1H), 5.93 (d, J=10.8 Hz, 1H), 2.56–2.18 (m, 4H), 0.87 (s, 9H), 0.19 (s, 3H), 0.11 (s, 3H).

¹³C NMR (CDCl₃) δ: 198.5–198.1 (b, —CO's), 193.3, 190.8, 150.9, 136.6, 127.4, 111.5, 100.4, 85.2, 73.9, 38.1, 25.9, 24.4, 18.5, −3.15, −3.35.

Preparation V. Alternative method for the preparation of compound E

Following the procedure described in Preparation II (a), a solution of the lithium enolate was prepared from 5 mmol of 7,7-diethoxy-1-trimethylsilyl-3-heptene-1,5-diyne. To this solution stirring at −78° C. in 85 mL of solvent was added 1.15 mL (50 mmol) of tertbutyldimethyl silyl trifluoromethanesulfonate. The reaction mixture was stirred for 15 min at −78° C. and then removed from the cooling bath and allowed to stir for an additional 25 min before being poured into a mixture of 100 mL water, 70 mL ethyl acetate, 25 mL diethyl ether, and 25 mL pentane. The mixture was extracted, and the aqueous layer was reextracted with 100 mL of 50:50 pentane/ethyl acetate. The combined organic extracts were washed with 75 mL saturated aqueous NaCl, dried over Na₂SO₄, concentrated in vacuo, and purified by flash chromatography on SiO₂ using and then 3% ethyl acetate/hexane as eluent to provide 1.47 g (51%) of the desired silylenol ether identical with material prepared in Preparation II (b).

Preparation VI. Alternative methods for the preparation of compound C (a) Alternative method A Following the procedure of Preparation II (a), a solution of the lithium enolate in 85 mL of solvent was prepared from 5 mmol of 7,7-diethoxy-1-trimethylsilyl-3-heptene-1,5-diyne. To this solution at −78° C. was added via syringe over a 2 min period a solution of phenylselenium chloride (0.99 g, 5 mmol) in 6 mL of dry tetrahydrofuran which had been precooled to −78° C. The reaction mixture was stirred for 20 min at −78° C., then the cooling bath was removed, and stirring continued for an additional 20 min. The reaction mixture was poured into 100 mL diethylether/100 mL ethyl acetate/100 mL water and extracted. The aqueous layer was reextracted with 50 mL 1:1 ethylether/ethyl acetate, and the combined organic extracts were washed with 75 mL saturated aqueous NaCl, dried over Na₂SO₄, and concentrated in vacuo. Flash chromatography on SiO₂ using 4% and then 5% ethyl acetate/hexane provided 1.68 g (57%) of a light brown liquid which was a mixture of phenyselenide, 2-[[(1,1-dimethylethyl)-dimethyl]silyl]oxy-2-(7,7-diethoxy-3-heptene-1,5-diynyl)-6-phenylseleno-cyclohexanone [compound H].

The crude mixture of selenides as dissolved in 10 mL of methylene chloride and 0.485 mL (6.0 mmol) of pyridine was added. The solution was cooled in an ice-water bath, and a solution of 0.82 mL (8 mmol) 30% hydrogen peroxide in 1 mL of water was added via syringe in one portion. The reaction mixture was stirred for 5 min, and the ice bath was removed. The reaction mixture was stirred for 25 min, and 0.25 mL of the same hydrogen peroxide (1 mmol) solution was added. The reaction mixture was stirred for 15 min, and 1.57 mL (7 mmol) of H₂O₂ solution was added. The reaction mixture was poured into 160 mL methylene chloride, 50 mL saturated aqueous NaHCO₃, and 50 mL water. The shaken mixture was filtered by suction to separate the emulsion, and the layers separated. The organic extracts were washed with 50 mL saturated aqueous NaCl, dried over Na₂SO₄, and filtered in vacuo. Flash chromatography using 4% EtOAc/Hexane provided the desired enone whose physical properties were consistent with the material obtained in Preparation II (c).

(b) Alternative method B

A 1.0M solution of lithium bis(trimethyl)silylamide in THF (28.7 mL, 28.77 mmol) was added to 30 mL of dry THF stirring under N₂, and the solution was cooled to −10° C. A solution of 1.54 g (13.7 mmol) 1,2-cyclohexanedione in 7 mL of THF was added in a slow stream via syringe. The reaction mixture turned darkreddish brown. The reaction mixture was stirred for 15 min at −10° C. and then cooled to −50° C. A solution of 4-methylphenyl 4-methyl-benzenethiosulfonate (3.5 g, 14.2 mmol) in 10 mL of THF at −50° C. was added in one portion via syringe. The reaction mixture was stirred for 2 h at −50° C. and allowed to warm at ambient temperature until approximately 0° C., and then 100 mL of 0.1 N HCl was added. The mixture was extracted with 300 mL and then 100 mL of diethyl ether, and the combined organic extracts were dried over anhydrous sodium sulfate. Concentration in vacuo provided a yellow solid which was purified by flash chromatography over silica gel using CH₂Cl₂, 10% EtOAc/Hexane, and then 3% MeOH/CH₂Cl₂ as eluent. The desired product, 2-hydroxy-3-[(4-methylphenyl)thio]-2-cyclohexenone [Compound Iy], was isolated as a white solid (1.939 g, 60%).

Anal. calcd. for C₁₃H₁₄O₂S:
C, 66.64; H, 6.02; N, 0.00.
Found: C, 66.63; H, 6.10; N, 0.00.
IR (KBr): 3372, 3054, 2954, 2920, 2870, 2834, 1642, 1600, 820, 656, 628 cm⁻¹.

¹H NMR (CDCl₃) δ: 7.38 (d, J=8.1 Hz, 2H), 7.16 (d, J=8.2 Hz, 2H), 6.47 (s, 1H, —OH), 2.44 (t, J=6.2 Hz, 2H), 2.35 (s, 3H), 2.17 (t, J=5.9 Hz, 2H), 1.87 (m, 2H).

¹³C NMR (CDCl³) δ: 191.1, 143.0, 140.3, 136.0, 133.5, 130.6, 126.3, 35.4, 28.3, 22.8, 21.5.

Tert butyldimethylsilyltrifluoromethanesulfonate (TBSOTf) (20.75 mL, 90.03 mmol) was added via syringe to a solution of compound Iy (17.64 g, 75.28 mmol) and Et₃N (15.7 mL, 112.92 mmol) stirring in 250 mL of methylene chloride under a nitrogen atmosphere at 2° C. After 5 min, the cooling bath was removed, and the reaction mixture was allowed to stir for 22 h. An additional 0.78 mL (5.59 mmol) of Et₃N followed by 0.865 mL (3.76 mmol) TBSOTf was added, and the reaction mixture was stirred for 2 h more. The reaction mixture was poured into 200 mL of water and 50 mL CH₂Cl₂ and extracted. The organic layer was washed with saturated aqueous brine, dried over Na₂SO₄, and concentrated in vacuo. Purification by flash chromatography over SiO₂ using a 0–10% EtOAc/hexane gradient as eluent provided 21.22 g (81%) as an off-white solid of 2-TBSoxy-3-[(4-methyl-phenyl)thio]-2-cyclohexenone [compound J].

¹H NMR (CDCl₃) δ: 7.38 (d, J=8.06 Hz), 2H), 7.15 (d, J=7.9 Hz, 2H), 2.35 (s, 3H), 2.38–2.34 (m, 2H), 2.12 (t, J=6.05 Hz, 2H), 1.82 (m, 2H), 1.00 (s, 9H), 0.21 (s, 6H).

A solution of 8.64 g (40 mmol) 80–85% pure MCPBA in 125 mL of dichloromethane at 25° C. was added via pipette to a solution of 12.7 g (36.4 mmol) compound J in 600 mL of dichloromethane at −78° C. The reaction mixture stirred for 1.75 h at −78° C. and poured into 1,100 mL of diethyl ether and 500 mL sat aq. Na$_2$SO$_3$. After extraction, the organic layer was washed successively with 300 mL and 200 mL portions of saturated aqueous NaHCO$_3$ and then dried over sodium sulfate. After removal of the solvent in vacuo, the crude product was purified by flash chromatography on SiO$_2$ using 10% and then 20% EtOAc/Hexane as eluent to provide 12.2017 g (92%) of the corresponding sulfoxide [compound K] as viscous, lightyellow oil.

Anal. calcd. for C$_{19}$H$_{28}$O$_3$SSi:
C, 62.59; H, 7.49; N, 0.00.
Found: C, 62.24; H, 7.49; N, 0.06.
IR (NaCl, Film): 2954, 2930, 2886, 2858, 1694, 1610, 1080 cm$^{-1}$.
$^1$H NMR (CDCl$_3$) δ: 7.48 (d, J=8.3 Hz, 2H), 7.28 (d, J=8.2 Hz, 2H), 2.82-2.74 (m, 1H), 2.55-2.46 (m, 1H), 2.38 (s, 3H), 2.38-2.29 (m, 1H), 2.05-1.86 (m, 3H), 0.98 (s, 9H), 0.32 (s, 3H), 0.20 (s, 3H).
$^{13}$C NMR (CDCl$_3$) δ: 195.5, 142.6, 141.6, 140.5, 0.6, 124.3, 38.3, 26.1, 22.4, 21.5, 19.2, 18.5, −3.4, −4.0.

Lithium bis(trimethylsilyl)amide (40 ml of 1.0 M solution in THF) was added via syringe to a solution of 7.13 g (40.0 mmol) of 7,7-diethoxy-3-heptene-1,5-diyne stirring in 250 mL dry THF at −78° C. under a nitrogen atmosphere. The dark solution was stirred for 30 min, and then a solution of 12.15 g (33.3 mmol) of compound K which had been precooled to −78° C. was added via cannula over 5 min. The reaction mixture was removed from the cooling bath and allowed to stir at ambient temperature for 1.6 h. The reaction mixture was poured into 500 mL 1N HCl and 1 L 1:1 ether:ethyl acetate and extracted. The aqueous layer was reextracted with two 150 mL portions of the same solvent, and the combined organic extracts were washed with 200 mL saturated aqueous NaCl and then dried over anhydrous Na$_2$SO$_4$. Purification by flash chromatography over SiO$_2$ using a gradient of 10-25% EtOAc/Hexane as eluent provided 15.5 g (86%) of a viscous brown liquid which was the desired product as a mixture of diastereomers [compound L].

IR (NaCl, Film): 2930, 2858, 2214, 2256, 1736, 1652, 1798, 1086, 1052 cm$^{-1}$.

A solution of 12.02 g (22.1 mmol) of compound L and 7.4 g (44.3 mmol) of 2-mercaptobenzothiazole in 100 g of heptyne was heated at reflux for 50 min, allowed to cool, and then poured into 400 mL diethyl ether and 400 mL water. The layers were separated and the organic layer dried over anhydrous sodium sulfate. Removal of most of the ether by rotary evaporation caused deposition of a brown precipitate which was removed by suction filtration and discarded. Purification of the filtrate by flash chromatography over silica gel in the usual manner provided 4.47 g (50%) of the desired enone which had the physical characteristics described previously.

(c) Alternative method C

Compound D (16.96 g, 41.91 mmol) was dissolved in 400 mL of dry THF and cooled to −78°. A 1.0 M solution of lithium bistrimethylsilylamide in THF (48 mL, 48 mmol) was added via syringe over about 2 minutes. The reaction mixture was stirred for four minutes and then the cooling bath was replaced with an ice water bath. The reaction mixture was stirred for 1.5h, and then allyl chloroformate (6.5 mL, 58.7 mmol) was added neat, quickly via syringe. The reaction mixture was stirred for 1.5h, poured into water, and extracted with three portions of ethyl acetate. The combined organic extracts were washed with saturated brine and then dried over anhydrous Na$_2$SO$_4$. Concentration and purification by flash chromatography over silica gel using 4% then 5% ethyl acetate/hexane as eluent provided the enol allylcarbonate (compound S, 16.97 g 84%) of a slightly yellow, clear oil.

$^1$H NMR (CDCl$_3$) δ: 5.97-5.80 (m, 3H), 5.53 (t, 4.0 Hz, 1H), 5.40-5.22 (m,3H), 4.61 (m,2H), 3.75-3.68 (m, 2H), 3.63-3.55 (m, 2H), 2.27-1.99 (m, 4H), 1.79 (m, 2H), 1.21 (t, J=7.1Hz, 6H), 0.82 (s, 9H), 0.179 (s,3H), 0.173 (s, 3H).
$^{13}$C NMR (CDCl$_3$) δ: 153.37, 147.20, 131.38, 120.24, 118.72, 118.52, 117.30, 98.68, 91.61, 91.48, 86.49, 82.07, 68.51, 68.11, 60.77, 40.47, 25.46, 23.84, 18.82, 17.87, 14.95, −3.13, −3.56.

Anal. calcd. for C$_{26}$H$_{40}$O$_6$Si: C, 66.36; H, 8.25; N, 0.00.
Found: C, 66.28; H, 8.31; N, 0.00.
IR (film on NaCl) 2932, 1766, 1682, 1650 cm$^{-1}$.

Acetonitrile (115 mL) was added to a flask containing Pd(OAc)$_2$ (0.1 g, 0.445 mmol) and compound S (16.47 g, 33.7 mmol) under an argon atmosphere and a reflux condenser. The reaction mixture was heated at reflux for 3h and then concentrated in vacuo. Purification by flash chromatography over silica gel using 4% then 5% ethyl acetate/hexane as eluent provided some non polar products and then 11.12 g (82%) of a colorless oil which was the desired compound C. The spectral data of this reaction product is the same as that reported in preparation C.

Preparation VII. Alternative method for the preparation of comoound G

(a) (Z) 5-chloro-1-(2-tetrahydropyranyloxy)-4-pentene-2-yne (compound M)

Tetrahydrofuran (degassed, 600 mL) was added via cannula to a flask containing 7.55g (39.6 mmol) CuI and 5.93 g (5.13mmol) tetrakis(triphenylphosphine)palladium(O) stirring under an argon atmosphere. Neat cis 1,2-dichloroethylene (50 g, 516 mmol) was added via syringe followed by 68 mL (688 mmol) of butylamine. 2-(3-propynyloxy)tetrahydropyran (48 g, 344 mmol) was added dropwise over 10 min. After the addition was complete the reaction mixture was stirred for 10 min and then cooled in an external ice water bath for 40 min. The cooling bath was removed and the rection mixture allowed to stir for 4h at ambient temperature (25° C.). Air was bubbled through the reaction mixture for 15 min and then the reaction mixture was filtered by suction through a glass frit using pentane then ether washes for transfer. The reaction was taken up in ethyl acetate and washed twice with water. The aqueous layers were reextracted with ethyl acetate and the combined organic layers dried over sodium sulfate, filtered and concentrated in vacuo. Flash chromatography over silica gel using 2.5% then 4% ethyl acetate/hexane as eluent provided 48.74 g (71%) of clear, slightly reddish liquid:

$^1$NMR (CDCl$_3$) δ: 6.33 (d,J=7.5 Hz,1H), 5.84 (m,1H), 4.80 (m,1H), 4.36(m,2H), 3.78 (m,1H), 3.48 (m,1H), 1.80-1.40 (m,6H).
$^{13}$C NMR (CDCl$_3$) δ 128.7, 111.6, 96.7, 93.5, 79.6, 62.0, 54.5, 30.2, 25.3, 19.0.
IR (NaCl film) 3084, 3026, 2944, 2870, 2854, 1592 cm$^{-1}$.

Anal. calcd. for $C_{10}H_{13}ClO_2$: C, 59.86; H, 6.53.
Found: C, 59.74; H, 6.44; N, 0.03.

(b) (Z) 7-(2-tetrahydropyranyloxy)-1-(trimethylsilyl)-3-heptene-1,5-diyne (compound N)

Degassed anhydrous tetrahydrofuran (500 mL) was added to 5.86 g (4.32 mmol) solid tetrakis(triphenylphosphine) palladium(O) and copper (I) iodide (5.17 g, 27.1 mmol) stirring under argon. A solution of the vinyl chloride (compound M of step (a) 45.38 g, 226.1 mmol) in 100 mL of dry tetrahydrofuran was added via cannula followed immediately by the addition of 45 mL (455 mmol) neat butylamine. The flask was wrapped in aluminum foil to exclude light and then 41.6 mL (294 mmol) of trimethylsilyl acetylene was added via syringe over 4 min. After about 10 min the reaction became very warm and was cooled in an ice water bath for 3 min. The cooling bath was then removed and the reaction allowed to stir for 4h at ambient temperature. Air was bubbled through the reaction for 15 min and then the reaction was filtered by suction through a glass frit using pentane then ether washes for transfer. The reaction was diluted with ether and washed with five 500 ml portions of water. The aqueous washes were reextracted with a small amount of diethyl ether and the combined organic extracts were dried over anhydrous $Na_2SO_4$, filtered, and concentrated on a rotary evaporator. Flash chromatography over $SiO_2$ using 2.5% to 4% ethyl acetate/hexane as eluent provided 52.86 g (89%) of liquid as the desired product:

$^1$HNMR (CDCl$_3$) δ 5.83 (m,2H), 4.86 (bs, 1H), 4.44 (ABq, Jab=14 Hz,2H), 3.82 (m,1H), 3.52 (m,1H), 1.89–1.49 (m,6H), 0.33(s,9H).

$^{13}$NMR (CDCl$_3$) δ 120.1, 119.7, 103.0, 101.7, 96.5, 93.4, 83.0, 61.8, 54.6, 30.2, 25.3, 18.9, −0.21.

IR (NaCl film) 2956, 2144, 844 cm$^{-1}$.

Anal.calcd for $C_{15}H_{22}O_2Si$:
C, 68.65; H, 8.45; N, 0.00.
Found: C, 68.79; H, 8.35. N, 0.06.

(c) (Z) 7-(2-tetrahydropyranyloxy)-3-heptene-1,5-diyne (compound-0)

Lithium hydroxide monohydrate (22.55 g, 0.54 mol) was added in one portion to a solution of 21.62 g (82.38 mmol) silyl diynene (compound N of step (b)) in 240 mL tetrahydrofuran and 40 mL water stirring at 25° C. The reaction was stirred for 1.58h and then diluted with 1:1 ether:hexane and water. The aqueous layer was reextracted with three portions of ether and then the combined organic extracts were dried over anhydrous sodium sulfate. Flash chromatography over silica gel using a gradient of 2.5 to 10% ethyl acetate/hexane as eluent provided 15.69 g (98%) of brown liquid:

$^1$HNMR (CDCl$_3$) δ 5.92 (d,J=11.0 Hz,1H), 5.78 (dd,J=11.1, 2.2 Hz,1H), 4.87 (m,1H), 4.45 (tallmultiplet, 2H), 3.83 (m,1H), 3.52 (m,1H), 3.30 (d,J=2.1Hz,1H), 1.79–1.48 (m,6H).

$^{13}$CNMR (CDCl$_3$) δ 121.2, 118.7, 96.6, 93.5, 84.7, 82.7, 80.5, 62.0, 54.6, 30.2, 25.4, 19.0.

IR (NaCl film) 3288, 2944, 2870, 2854, 2096 cm$^{-1}$.
Anal calcd for $C_{12}H_{14}O_2$=C, 75.76; H, 7.42.
Found=C, 75.22; H, 7.30.

(d) (Z) 6-[[(1,1-dimethylethyl)dimethylsilyloxy]-6-[7(2-tetrahydropyranyloxy)-3-heptene-1,5-diynyl]-2-cyclohexenone (compound P)

A 1.0M solution of lithium bis(trimethylsilylamide) in tetrahydrofuran (89 mL, 89 mmol) was added via syringe to a solution of 15.4 g (80.9 mmol) diynene (compound O of step (c)) in 500 mL of tetrahydrofuran stirring at −78° C. under an atmosphere of nitrogen. The reaction was stirred for 35 min and then a solution of 24.6 g (67.46 mmol) sulfoxide ketone (compound K) in 100 mL of tetrahydrofuran at −70° C. was added via cannula. The cooling bath was removed and the reaction was allowed to stir at ambient temperature for 2h (gradually reaching 25° C.). The reaction was quenched with saturated aqueous ammonium chloride and extracted with two portions of 1:1 ethyl acetate:ethyl ether. The combined organic extracts were washed with saturated aqueous sodium bicarbonate then saturated sodium chloride, dried over sodium sulfate, and concentrated in vacuo. Purification by flash chromatography over silica gel using a gradient of 2.5 to 20% ethyl acetate/hexane as eluent provided 27.3 g (73%) of viscous oil which was the desired keto sulfoxides as a mixture of diastereomers.

A solution of 27.3 g (49.2 mmol) of the sulfoxide from above in 540 mL of pyridine was heated at 105° C. for 1.75h and then diluted with toluene (several portions were added to help remove the pyridine azeotropically) and concentrated on a rotary evaporator. The crude product was purified by flash chromatography using 5 then 10% ethyl acetate/hexane as eluent to provide 18.0 g (88%) of a light yellow oil which was the desired product contaminated with trace amounts of sulfur byproducts. This material was used directly in the next alcohol deprotection reaction:

$^1$HNMR (CDCl$_3$) δ 6.89–6.82 (m,1H), 5.96 (dd,J=10.9,1.2Hz,1H), 5.87–5.77 (m,2H), 4.78 (m,1H), 4.46–4.31 (m,2H), 3.81(m,1H), 3.51 (m,1H), 2.70–2.64 (m,1H), 2.47–2.39 (m,1H), 2.29–2.14 (m,2H), 1.81–1.49 (m.6H), 0.68 (s,9H), 0.20 (s,3H), 0.18 (s,3H).

(e) (Z) 6-[[(1,1-dimethylethy)dimethylsilyl]-6-[(7-hydroxy)-3-heptene-1,5-diynyl]-2-cyclohexenone (compound Q)

Para-toluenesulfonic acid (1.21 g, 6.36 mmol) was added to a solution of the tetrahdropyranyl ether (compound P of step (d) 18.0 g, 43.3 mmol) in 200 mL of methanol stirring at 25° C. The reaction was stirred for 30 min and then concentrated on a rotary evaporator. The crude oil was taken up in ethyl acetate and washed with saurated aqueous $NaHCO_3$ and then saturated aqueous NaCl. The organic extracts were dried over anhydrous sodium sulfate and then concentrated in vacuo. Purification by flash chromatography over silica gel using a gradient of 5%–20% ethyl acetate/hexane as eluent provided 10.75 g (75%) of the desired product as a light yellow oil:

$^1$HNMR (CDCl$_3$) δ 6.91 (m,1H), 5.98 (dt,J=10.3,1.9 Hz,1H), 5.88 (dt,J=10.8,0.6 Hz,1H), 5.80 (d,J=10.7 Hz,1H), 4.40 (d,J=6.2 Hz,2H), 2.51–2.20 (m,4H), 1.59 (s.1H), 0.85 (s,9H), 0.20 (s,3H), 0.18 (s,3H).

$^{13}$C NMR (CDCl$_3$) 194.3, 150.7, 127.0, 121.0, 119.0 95.9, 94.3, 84.8, 82.6, 72.9, 51.3, 38.3, 25.5, 24.5, 18.0, −3.5, −3.6.

(f) Cobalt, hexacarbonyl [μ-[6-[(5,6η:5,6η)-(Z) 6-[[(1,1-dimethylethy)dimethylsilyl]-6-[(7-hydroxy)-3-heptene-1,5-diynyl]-2-cyclohexenone, di(Co-Co) (compound R)

Octacarbonyldicobalt (Alfa, 4.41 g, 12.9 mmol) was added in one portion to a solution of 4.27 g (12.9 mmol) enone alcohol (compound Q of step (e)) stirring in 170 mL of dichloromethane at 25° C. under an atmosphere of nitrogen. The reaction was stirred for 2h and then concentrated on a rotary evaporator. Purification by flash chromatography over silica gel using a gradient of 5 to 20% ethyl acetate/hexane provided 6.18 g (78%) of the desired product as a purple oil:

$^1$H NMR (CDCl$_3$) δ 6.91 (m,1H), 6.72 (d,J=10.7 Hz,1H), 6.01 (broad doublet,J=10.1 Hz,1H), 5.77 (d,J=10.6 Hz, H), 4.85 (d,J=6.5 Hz,2H), 2.56–2.30 (m,2H), 2.27 (t,J=5.6 Hz,2H), 1.50 (bs,1H), 0.85 (s,9H), 0.19 (s,3H), 0.074 (s,3H).

A slower eluting minor isomer (1.29 g, 16%) was also isolated and is the cobalt complex of the other acetylene of the diynene.

(g) Comoound G

A 2.0 M solution of ethylmagnesium bromide in tetrahydrofuran (6.50 mL, 13 mmol) was added dropwise to a solution of t-butanal (1.29 mL, 13.5 mmol) in 30 mL of dry tetrahydrofuran at 0° C. The reaction was stirred for 15 min and then the cooling bath was removed. After 5 min a solution of the cobalt complexed alcohol (compound R of step (f) 6.18 g, 10.03 mmol) was added via cannula. A solution of 3.39 g (13.4 mmol) 1,1'-(azodicarbonyl)dipiperidine in 30 mL dry tetrahydrofuran was added dropwise via cannula. After the addition was complete the reaction was poured into a saturated aqueous brine solution and extracted. The organic layer was washed with saturated aqueous sodium bicarbonate and then saturated aqueous brine. The combined aqueous washes were extracted once with 1:1 ethyl acetate: ethyl ether and then the combined organic extracts were dried over anhdrous sodium sulfate and concentrated in vacuo. Flash chromatography using 10% ethyl acetate/hexane provided 5.57 g (89%) of reddish purple viscous oil.

Preparation VIII. Preparation of dimethylphenylthiol aluminum

A solution of 1.0 mL of 2.0 M trimethylaluminum in hexanes was added dropwise over 0.5 min to a solution of 0.2054 mL (2.0 mmol) thiophenol stirring in 2 mL dry hexane under a nitrogen atmosphere in an ice water cooling bath.

The reaction mixture was stirred for 30 min, and then 6 mL of dry tetrahydrofuran was added via syringe.

Preparation X. Preparation of 2-quinoxalyl isocyanate

Diphenylphosphoryl azide (1.23 mL) was added to a solution of triethylamine (800 ul) and 2-quinoxaline carboxylic acid 1 g (5.74 mmol) stirring in 10 mL of dry dimethylformamide in an icewater cooling bath (2°). The reaction was stirred for 2.33h during which time the reaction was allowed to warm to 25°. The reaction was poured into ice water and extracted three times with diethyl ether. The combined organic extracts were dried over anhydrous sodium sulfate, filtered, and then concentrated in vacuo. The crude azide was dissolved in 15mL of benzene and heated at reflux for 1.5h. The solvent was removed in vacuo to provide the desired solid isocyanate. FT IR indicated a strong isocyanate absorption.

The following examples are provided to more fully illustrate the invention and are not to be construed as limiting the scope of the invention in any manner.

EXAMPLE 1.

Cobalt, hexacarbonyl[μ-(6,7-η)-1-[[(1,1-dimethylethyl) dimethylsilyl]oxy]-8-hydroxy-10-phenylthio-bicyclo[7.3.1tridec-4-ene-2,6-divn-13-one]] di (Co-Co)

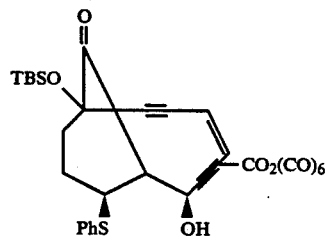

A previously prepared stock solution of dimethyl(-phenylthio)aluminum (6.85 ml, 1.49 mmol) was added in one portion via syringe to a solution of enone cobalt complex aldehyde (compound G, 297 mg, 0.483 mmol) in 11 mL of dry tetrahydrofuran stirring under a nitrogen atmosphere at −50° C. The reaction mixture was stirred for 15 min and then cooled to −78° C. The reaction mixture was then allowed to warm to −50° C. over 90 min, and neat titanium isopropoxide (1.0 mL, 3.34 mmol) was added thereto in one portion via syringe. The reaction mixture was stirred for 15 min at a temperature between −50° C. and −45° C., and then an additional 2.0 mL (6.68 mmol) of neat titanium isopropoxide was added. The reaction mixture was stirred for 15 min between −50° and −45° C. and then 20 min between −45° and −40° , and then an additional 2.0 mL (6.68 mmol) of titanium isopropoxide was added. The reaction mixture was stirred for 15 min between −40° C. and −30° C. and then recooled to −65° . The reaction mixture was allowed to warm to −55° over 30 min, and then the cooling bath was removed. The reaction mixture was stirred for 20 min at ambient temperature and then poured into 300 ml of ethyl acetate and 100 mL of water and extracted. The aqueous layer was reextracted with 100 ml of ethyl acetate, and the combined organic layers were washed with 100 ml saturated aqueous NaCl solution and then dried over anhydrous Na$_2$SO$_4$. After filtration and concentration in vacuo, the crude product was purified by flash chromatography on SiO$_2$ to provide four fractions of material described in their order of elution from the column:

Fraction 1 contained 56 mg (16%) of purple viscous oil which was an aldehyde resulting from simple conjugate addition of phenylmercaptan; fraction 2 contained 68.2 mg (23%) of pure recovered starting material; and fraction 3 contained a 6:4 mixture of the desired product and starting material (59 mg, 11% desired, 6% starting material).

Fraction 4 provided 142 mg (41%) of the desired title compound as a reddish-purple foam.

IR (KBr): 3442, 3060, 2954, 2930, 2894, 2858, 2096, 2060, 2029, 1730, 1080, 838, 780, 744 cm$^{-1}$.

$^1$H NMR (CDCl$_3$) δ: 7.50–7.47 (m, 2H), 7.36–7.24 (m, 3H), 7.03 (d, J=9.9 Hz, 1H), 5.79 (d, J=9.9 Hz, H), 5.29 (bt, J=7.5 Hz, 1H), 4.32 (bs, 1H), 2.77 (d, J=9.2 Hz, 1H), 2.51–2.38 (m, 2H), 2.28–2.27 (m, 1H), 1.98–1.93 (m,

1H), 1.38 (d, J=7.5 Hz, 1H, —OH), 0.83 (s, 9H), 0.19 (s, 3H), 0.13 (s, 3H).

$^{13}$C NMR (CDCl$_3$) δ: 199.1 (b), 198.3, 142.4, 133.7, 129.7, 128.4, 110.5, 99.2, 97.4, 92.1, 82.6, 69.4, 62.6, 48.5, 37.1, 25.9, 23.4, 18.5, −2.6, −2.9.

EXAMPLE 2

Example
8-Hydroxy-1-TBSoxy-bicvclo[7.3.1]trideca-4,9-diene-2,6-diyn-13-one

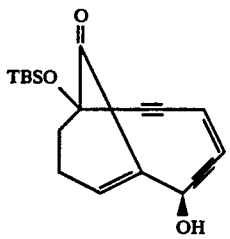

(a) Preperation of
1-[[((1,1-dimethylethyl))dimethylsilyl]oxy]-8-hydroxy-10-phenylthio-bicyclo[7.3.1]tridec-4-ene-2,6-diyn-13-one

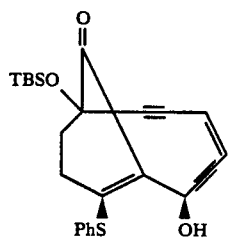

Iodine crystals (12 mg, 0.095 mmol) were added to a solution of cobalt complex reaction product of Example 1 (19 mg, 0.026 mmol) in 5 mL of dry benzene stirring under a nitrogen atmosphere at 25° C. The reaction mixture was stirred for 2 h, concentrated slightly in vacuo, and then flash chromatographed on SiO$_2$ using 4% ethyl acetate/hexane as eluent to provide 6 mg (53%) of the desired decomplexed substrate as a clear oil.

FAB MS (NOBA): M+ 438.

IR Neat (NaCl, Film): 3484, 3060, 2954, 2958, 2208(w), 1714, 584 cm$^{-1}$.

$^1$H NMR (CDCl$_3$) δ: 7.48–7.38 (m, 2H), 7.36–7.31 (m, 3H), 5 92 (s, 2H), 5.25 (dd, J=11.0, 4.5 Hz, 1H), 4.43 (d, J=11.0 Hz, 1H, —OH), 4.05 (dt, J=5.5, 9.8 Hz, 1H), 2.81 (dd, J=10.1, 4.6 Hz, 1H), 2.43 (m, 1H), 2.29 (m, 1H), 2.10 (m, 1H), 1.91 (m, 1H), 0.88 (s, 9H), 0.19 (s, 3H), 0.17 (s, 3H).

$^{13}$C NMR (CDCl$_3$) δ: 207.1, 134.7, 132.6, 129.8, 129.0, 125.1, 123.6, 99.6, 98.0, 92.9, 85.0, 74.4, 65.7, 59.1, 43.1, 34.7, 26.9, 25.9, 18.4, −2.9, −3.0.

(b) preparation of
1-[[(1,1-dimethylethyl)dimethylsilyl]-oxy]-8-hydroxy-bicyclo[7.3.1]trideca-4,9-diene-2,6-diyn-13-one Solid sodium periodate (120 mg, 0.56 mmol) was added to a solution of the product of step (a) above (5 mg, 0.011 mmol) in 5 mL methanol and 2 mL water at 25° C. The reaction mixture was stirred for 10 min, and 1 mL of water was added to dissolve the precipitate, and the stirring continued for 90 min. An additional 149 mg (0.70 mmol) of sodium periodate was added, and the reaction mixture stirred for 45 min and extracted with 50 mL of methylene chloride and 5 mL of water. The aqueous layer was reextracted with 10 mL of methylene chloride. The combined organic layers were dried over anhydrous Na$_2$SO$_4$, concentrated in vacuo, and flash chromatographed on SiO$_2$ using 10% ethyl acetate/hexane as eluent to provide two fractions:

Fraction 1 provided less than 1 mg of a minor, faster eluting side product. Fraction 2 provided 2 mg (56%) of the desired title compound as a white solid.

FAB MS (NOBA): (M+H) 329.

IR Neat (NaCl) 3356, 2952, 2928, 2856, 1712, 1690, 1414, 782 cm$^{-1}$.

$^1$H NMR (CDCl$_3$) δ: 6.37 (bs, 1H), 5.84 (s, 2H), 5.22 (d, J=10.8 Hz, 1H), 4.82 (d, J=10.8 Hz, 1H, —OH), 2.51–2.47 (m, 2H), 2.28–2.25 (m, 1H), 2.16–2.10 (m, 1H), 0.91 (s, 9H), 0.22 (s, 3H), 0.19 (s, 3H).

$^{13}$C NMR (CDCl$_3$) δ: 196.8, 139.4, 137.2, 124.8, 123.1, 101.4, 96.3, 93.0, 87.7, 74.6, 69.2, 34.6, 26.0, 24.8, 18.5, −2.8, −3.1.

EXAMPLE 3

Alternative preParations of compound of Example 2

(a) Alternative method A

Solid 3-chloroperbenzoic acid, (mCPBA, 10.3 mg, 0.059 mmol) was added to a solution of the product of Example 1 (23.4 mg, 0.032 mmol) in 10 ml of methylene chloride at 25° C. The reaction mixture was stirred for 15 min, and an additional 14.9 mg (0.086 mmol) was added. The reaction mixture was stirred for another hour during which 6.2 mg (.035 mmol) more of mCPBA was added. The reaction mixture was poured into approximately 20 ml of methylene chloride and 10 ml of saturated solution of NaHCO$_3$. The aqueous layer was extracted with methylene chloride and the organic layer washed with saturated solution of NaCl, and the combined organic layer was dried over anhydrous Na$_2$SO$_4$ and concentrated in vacuo. Flash chromatography on SiO$_2$ using 5% ethylacetate/hexane as eluent provided 4.6 mg (43%) of the desired product as an off-white solid.

(b) Alternative method B

A solution of 0.595 g (3.45 mmol) of 85% pure MCPBA in 15 mL of CH$_2$Cl$_2$ was added dropwise via pipet to a solution of 2.0 g (2.76 mmol) of the product of Example 1 in 100 mL of CH$_2$Cl$_2$ stirring at −78° under a nitrogen atmosphere. The reaction mixture was stirred for 30 min at −78° and then removed from the cooling bath. Immediately, 50 mL of 1-hexyne was added and then the reaction mixture was allowed to stir for 1.33 h at ambient temperature. The reaction mixture was then poured into a mixture of 400 mL CH$_2$Cl$_2$, 200 mL water, and 100 mL sat. aq. NaHCO$_3$. After extraction the aqueous layer was reextracted with two 150 mL portions of CH$_2$Cl$_2$ The combined organic extracts were washed with 200 mL of saturated brine, dried over sodium sulfate, and concentrated in vacuo. The resulting red oil was dissolved in 60 mL of acetone which contained 0.15 mL (1.08 mmol) of triethylamine. A single portion of cerric ammonium nitrate (CAN, 4.5 g, 8.21 mmol) was added and the reaction was stirred for 35 min. An additional 1.00 g (1.82 mmol) of CAN was added and the reaction mixture was stirred for 15 min longer. The reaction mixture was poured into 500 mL of ethyl acetate and 200 mL of water and extracted. The aqueous layer was reextracted with three 100 mL portions of ethyl acetate and then the combined organic extracts were washed with 100 mL sat. aq. brine. The solution was dried over sodium sulfate, filtered, concentrated in vacuo and placed on top of a 8 inch×1.7 inch flash column of silica gel. Elution with 3-10% ethyl acetate/hexane provided, after concentration in vacuo, 504 mg (56%) of the desired enone as a white solid.

EXAMPLE 4

1,8-Dihydroxy-bicyclo7.3.1]trideca-4,9-diene-2,6-divn-13-one (a) Alternative method A

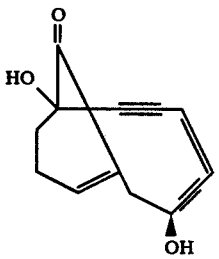

Trifluromethanesulfonic acid (2 drops from a 22 gauge needle, 0.010 mL, 0.11 mmol) was added to a solution of 8-hydroxy-1-TBSoxy-bicyclo[7.3.1]trideca-4,9-diene-2,6-diyn-13-one (product of Example 2, 12.2 mg, 0.040 mmol) in 7 mL of dichloromethane containing 800 mg of 4A molecular sieves stirring at 25° C. The reaction mixture was stirred for 10 minutes, diluted with 50 mL dichloromethane, and washed with 50 mL of saturated aqueous sodium bicarbonate. The organic layer was concentrated in vacuo. The crude product thus obtained was combined with the crude product from a similar experiment in which 2.5 mg of the enone alcohol was utilized. Flash chromatography of the combined crude product over silica gel using 10% and then 20% ethyl acetate/hexane as eluent provided 8.6 mg (83%) of the desired product as a white stable solid.

MS: m/e 214.

$^1$H NMR (CDCl$_3$) $\delta$: 6.51 (m, 1H), 5.84 (s, 2H), 5.23 (d, J=11.2 Hz, 1H), 4.38 (d, J=11.2 Hz, 1H, —OH), 3.93 (s, 1H, —OH), 2.58-2.51 (m, 2H), 2.46-2.39 (m, 1H), 2.13-2.01 (m, 1H).

$^{13}$C NMR (CDCl$_3$) $\delta$: 195.8, 141.1, 135.8, 124.3, 122.9, 100.2, 95.7, 91.5, 87.6, 72.0, 68.4, 31.4, 24.1.

Anal. calcd. for C$_{13}$H$_{10}$O$_3$: C, 72.89,; H, 4.71
Found: C, 73.06; H, 4.95.

(b) Alternative method B

A 48% aqueous solution of HF (0.5 mL) was added to a stirred solution of 15 mg (0.046 mmol) of silyl enone in 1.5 mL of CH$_2$CN at 25° under a nitrogen atmosphere. The reaction mixture was stirred for 5 min at 25°. TLC (20% EtOAc/hexane on SiO$_2$) showed only starting material. The reaction mixture was heated to reflux and then refluxed for 5 min. The heat source was then removed and the reaction mixture was allowed to stir for 15 min at ambient temperature. The reaction mixture was poured into 40 mL of CH$_2$Cl$_2$ and 40 mL water. The mixture was extracted and the aqueous layer was reextracted with an additional 20 mL portion of CH$_2$Cl$_2$. The extracts were washed with 20 mL of saturated aqueous brine, dried over sodium sulfate, and concentrated in vacuo. Flash chromatography on SiO$_2$ using 30% then 50% diethyl ether/pentane as eluent provided 8.7 mg (89%) of a white solid which was the desired desilylated diol.

EXAMPLE 5

8-Acetoxy-1-hydroxy-bicyclo[7.3.1]trideca-4,9-diene-2,6-diyn-13-one

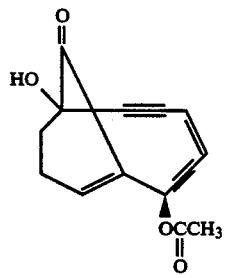

To a solution of 1,8-dihydroxy-bicyclo[7.3.1]-trideca-4,9-diene-2,6-diyn-13-one (product of Example 4, 32 mg, 0.149 mmol) in 1 ml of pyridine was added dimethylaminopyridine and 1 eq of acetic anhydride (14 ul, 0.149 mmol). The reaction mixture was stirred at ambient temperature for 30 minutes and then pyridine was stripped off on rotovap and on high vacuum. This residue was purified on a silica gel column using 10% and 20% ethyl acetate/hexane mixture as the solvent system. The title compound was obtained as light yellow foam in 85% yield (32.4 mg).

IR (KBr): 3450, 3058, 2926, 2856, 2196, 1742, 1710, 1634, 1418, 1342

$^1$H NMR(CDCl$_3$) $\delta$ 2.07 (1H, m), 2.18 (3H, s), 2.43 (1H, m), 2.56 (2H, m), 4.12 (1H, s), 5.86 (2H, q), 6.11 (1H, s), 6.69 (1H, t)

$^{13}$C NMR(CDCl$_3$) $\delta$ 21.069, 24.410, 32.090, 68.547, 72.456, 90.591, 90.822, 96.120, 97.016, 123.980, 124.846, 134.952, 143.671, 171.210, 192.392

MS: 257 (M+), 239, 215, 169

EXAMPLE 6

1-Hydroxy-8-[[(2-quinoxoly)carbonyl]oxy]-bicyclo[7.3.1trideca-4.7-diene-2.6-divn-13-one

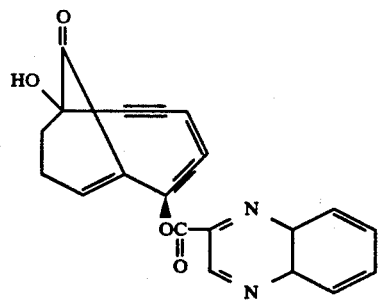

Solid 2-quinoxaloyl chloride (25 mg, 0.13 mmol) was added to a solution of 4-(N,N-dimethylamino)pyridine (32 mg, 0.26 mmol) and the product of Example 4 (19 mg, 0.089 mmol) in 2 mL pyridine stirring at 25° under an atmosphere of N$_2$. The reaction mixture was stirred for 30 min and then an additional 25 mg (0.13 mmol) of the acid chloride was added. The reaction mixture was stirred for another hour and then poured into 100 mL of ethyl acetate and 50 mL of water. The mixture was extracted and the aqueous layer was rextracted with two 25 mL portions of ethyl acetate. The combined organic extracts were washed with 50 mL sat. aqueous brine and dried over sodium sulfate. Concentration in vacuo followed by flash chromatography over silica gel using a 20–50% ethyl acetate/hexane gradient provided the title compound (29 mg 88%) as a white solid:
DCI MS: MH+ =371
IR (KBr) 3470(b), 2194, 1726, 1696, 1228 cm$^{-1}$.
$^1$H NMR (CDCl$_3$) δ: 9.68 (bs,1H), 8.34 (d, J=7.9 Hz, 1H), 8.20 (d, J=8.0 Hz, 2H), 7.89 (m, 2H), 6.84 (bs, 1H), 6.53 (s, 1H), 5.94 (ABq, J$_{AB}$=9.61 Hz, 2H), 4.13 (bs, 1H), 2.66–2.61 (m, 2H), 2.51 (m, 1H), 2.16–2.05 (m, 1H).
$^{13}$C NMR (CDCl$_3$) δ: 192.16, 189.74, 145.98, 144.09, 134.60, 133.14, 131.60, 130.08, 125.30, 123.95, 97.12, 95.49, 91.76, 90.65, 72.49, 69.99, 32.14, 24.52.

EXAMPLE 7

1-Hydroxy-8-[[(2,2,2-trichloroethoxy)carbonyl]oxy]-bicyclo[7.3.1]trideca-4,9-diene-2,6-divne-13-one

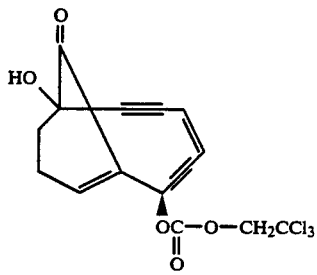

To a solution of the product of Example 4 (7.3 mg, 0.034 mmol) in 500 ul of pyridine was added trichloroethyl chloroformate (5 ul, 0.03 mmol). Additional trichloroethyl chloroformate and pyridine (500 ul) were added. The reaction mixture was stirred at ambient temperature for 1 hour and 10 minutes, washed with saturated solution of sodium chloride, and the aqueous layer extracted 3 times with methylene chloride. The combined organic layer was dried over sodium sulfate and concentrated in vacuo. The residue was purified on a silica gel column using ethyl acetate/hexane as the solvent system to yield the title compound (3.3 mg, 25% yield).
$^1$H NMR (CDCl$_3$): 2.08 (1H, m), 2.40 (1H,m), 2.60 (2H, m), 4.11 (1H, s), 4.78 (2H, d), 5.91 (2H, dd), 6.06 (1H, s), 6.69 (1H, t)
MS: 97, 169

EXAMPLE 8

1-Hydroxy-8-[[(2-quinoxolyamino)carbonyl]oxy]-bicyclo[7.3.1]trideca-4,7-diene-2,6-divn-13-one

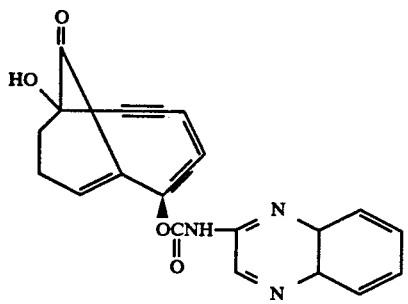

To a solution of 8-hydroxy-1-TBSoxy-bicyclo[7.3.1]-trideca-4,9-diene-2,6-diyn-13-one (product of Example 2, 137 mg, 0.419 mmol) in 10 ml of pyridine was added in portions 2.8 eq of quinoxaline-2-isocyanate (prepared by the method described in), first 140 mg, then 60 mg in an additional 2 ml of pyridine. To this was added dimethylamino pyridine (25 mg, 0.2 mmol). The reaction mixture was stirred at ambient temperature under nitrogen for 4 hours, washed with water, and the aqueous layer extracted twice with diethyl ether. The combined organic layer was dried over sodium sulfate and concentrated in vacuo. This residue was purified on a silica gel column using a gradient of 5% to 20% ethyl acetate/hexane mixture as the solvent system. The 1-TBS protected title compound was obtained as a yellow powder in 74% yield (44.1 mg, based on recovered starting material).

A solution of the 1-TBS protected title compound (40 mg, 0.08 mmol) in 16 ml of anhydrous methylene chloride and 1.8 g 4Å molecular sieves was stirred at ambient temperature under nitrogen for 10–15 minutes. To this mixture was added 2.8 eq of trifluoromethanesulfonic acid (first 15 ul, then 5 ul, 0.226 mmol). The reaction is complete upon addition of the trifluoromethanesulfonic acid. Saturated solution of sodium bicarbonate was added to the reaction mixture and the aqueous layer was extracted three times with methylene chloride. The combined organic layer was washed with saturated solution of sodium chloride, dried over sodium sulfate and concentrated in vacuo.

The solid residue was then triturated with 5% ethyl acetate/hexane mixture. The title compound was obtained as light yellow crystals and film in 97% yield (30.4 mg).
$^1$H NMR (CDCl$_3$): 2.07 (1H, m), 2.47 (1H, m), 2.61 (2H, m), 4.23 (1H, s), 5.89 ( 2H, q), 6.26 (1H, s), 6.76 (1H, t), 7.65 (2H, m), 7.84 ( 1H,d), 8.04 (1H, d), 9.62 (1H, s)

EXAMPLE 9

1-Hydroxy-8-[[(3-pvridylamino)carbonyl]oxy]bicyclo[7.3.1]trideca-4,9-diene-2,6-divne-13-one

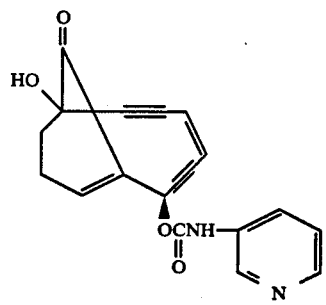

Pyridine 3-isocyanate (disclosed in U.S. Pat. No. 3,342,545, 56 mg, 0.464 mmol) was added to a solution of the product of Example 4 (28.9 mg, 0.135 mmol) in 4 mL of dry benzene. The reaction vessel was placed in an oil bath and the bath temperature was raised from 25° to 90° over 15 min. The reaction mixture was stirred for 1.1 h and then an additional 15 mg (0.125 mmol) of pyridine 3-isocyanate was added. The reaction mixture was stirred for 0.9 h more and then concentrated in vacuo. Purification over silica gel using a diethyl ether/hexane gradient as eluent provided the title compound (17.9 mg) as an offwhite solid.
$^1$H NMR (drop DMSO-d$_6$ in CDCl$_3$) δ 9.59 (bs, 1H), 8.56 (bs, 1H), 8.08 (bs, 1H), 7.75 (d, J=6Hz, 1H), 7.03

(m, 1H), 6.56 (m, 1H), 6.05 (s, 1H), 5.75 (d, J=10.4Hz, 1H), 5.66 (dd, J=1.1, 10.4Hz, 1H), 4.76 (bs, 1H), 2.21 (m,2H), 2.24 (m, 1H), 1.89 (m, 1H).

EXAMPLE 10

1-Hydroxy-8-[[(N,N-diethlyamino)carbonyl]oxy]bicyclo[7.3.1-trideca-4,9-diene-2,6-divne-13-one

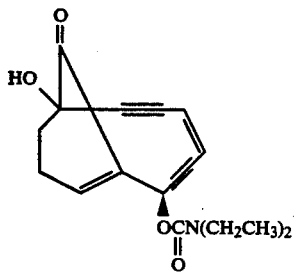

A solution of 1.90 M phosgene in toluene (0.1 mL) was added to a stirtred solution of the product of Example 2 (12.5 mg, 0.038 mmol) and 26.5 ul (0.19 mmol) triethylamine in 1.5 mL CH$_2$Cl$_2$ at 25°. The reaction mixture was stirred for 1.5h and then 25 ul (0.238 mmol) of diethylamine was added. After 10 min, the reaction mixture was poured into CH$_2$Cl$_2$ and water and extracted three times with methylene chloride. The combined organic extracts were washed with aqueous brine, dried over Na$_2$SO$_4$, and concentrated in vacuo to provide a tan solid.

The tan solid was dissolved in 6 mL of dry tetrahydrofuran and (25 ul, 0.025 mmol) of a 1.0 M solution of tetra n-butylammonium fluoride in tetrahydrofuran was added. The reaction began to darken immediately but was allowed to stir for 1h. The reaction ( mixture was poured into CH$_2$Cl$_2$ and water and extracted. The aqueous layer was reextracted once with dichloromethane and once with ether and then the combined organic extracts were dried over sodium sulfate. The reaction was concentrated in vacuo and purified by flash chromatography over silica gel to provide 2 mg of carbamate which was still silylated and a second fraction which contained mainly the title compound. This material was filtered through a small pad of silica gel to provide after concentration in vacuo 2.3 mg of white solid.

$^1$H NMR (CDCl$_3$) δ 6.65 (m, 1H), 6.15 (s,1H), 5.85 (ABq, JAB=8.2 Hz, 2H), 4.12 (s, 1H), 3.39–3.29 (m, 4H), 2.55 (m,1H), 2.50–2.39 (m,1H), 2.10–2.00 (m,2H), 1.19 (t, J=7.69 Hz, 3H), 1.11 (t, J=7.03 Hz, 3H)

EXAMPLE 11

1-Hydroxy-8-[[(methylamino)carbonyl]oxy]bicyclo[7.3.1]trideca-4,9-diene-2,6-diyne-13-one

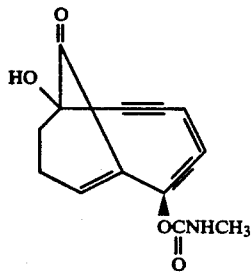

To a solution of the product of Example 2 (10.4 mg, 0.032 mmol) in 800 ul of pyridine was added methyl isocyanate (11 ul, 0.19 mmol) and dimethylaminopyridine. The reaction mixture was stirred at ambient temperature for about 3 hours at which time additional methyl isocyante (15 ul, 026 mmol) as added. The reaction mixture was stirred overnight (23 hours) at ambient temperature, washed with water, and the aqueous layer extracted twice with methylene chloride and once with ether. The organic layer was dried over sodium sulfate and then concentrated in vacuo. The residue was then purified on a silica gel pipet column and eluted with 5%, 10%, 20%, 35% ethyl acetate/hexane to provide the 1-TBS protected title compound (3.8 mg, 31% yield).

To a solution of the 1-TBS protected title compound (3.8 mg, 0.009 mmol) in 4 ml of methylene chloride was added 600 mg of 4A molecular sieves, and the mixture was stirred for 10 minutes at ambient temperature. To this was added trifluoromethanesulfonic acid (2 ul, 0.022 mmol) and the reaction was stopped immediately with a saturated solution of sodium bicarbonate. The aqueous layer was extracted twice with methylene chloride and the organic layer was then washed with saturated solution of sodium chloride, dried over sodium sulfate and concentrated in vacuo. The residue was purified on a silica gel column and eluted with 5%, 10%, 20%, 35% ethyl acetate/hexane to provide the title compound in nearly quantitative yield (3.2 mg).

$^1$H NMR (CDCl$_3$): 2.05 (1 H,m), 2.45 (1H, m), 2.57 (2H, m), 2.80 (3H, d), 4.12 (1H, s), 4.93 (1H, bs), 5.86 (2H, dd), 6.16 (1H, s), 6.69 (1H, t)

MS: 272 (MH+), 254, 228, 215, 197, 187, 169, 154, 141

EXAMPLE 12

1-Hydroxy-8-[[[(t-butoxycarbonyl)amino]pentyl aminocarbonyl]oxy]-bicyclo[7.3.1]trideca-4,9-diene-2,6-divne-13-one

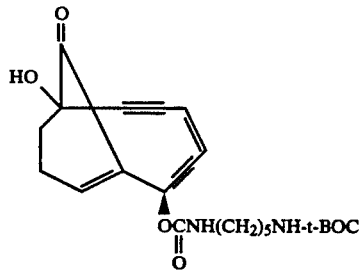

To a solution the product of Example 2 (20.3 mg, 0.06 mmol) in 1 ml of pyridine was added a solution of 5-(t-BOC amino)-pentylisocyanate in 500 ul of pyridine and dimethylamino pyridine. The reaction mixture was stirred at ambient temperature for 3 hours, washed with water, and the aqueous layer extracted 4 times with methylene chloride. The organic layer was dried over sodium sulfate and concentrated in vacuo. The residue was purified by flash column chromatography on a silica gel column and eluted with 5%, 10%, 20% ethyl acetate/hexane. The 1-TBS protected title compound was obtained as a yellow oil in 90% yield (31 mg).

The 1-TBS protected title compound (10.3 mg, 0.018 mmol) was dissolved in 1.2 ml of tetrahydrofuran. To this solution was added 6 ul of acetic acid and of tetrabutylammonium fluoride (10 ul, 0.01 mmol). Additional tetrabutylammonium fluoride (190 ul, 0.19 15 mmol) was added over a 45 minutes period. The reaction mixture was washed with water and the aqueous layer extracted 3 times with ether. The organic layer was dried over sodium sulfate and concentrated in vacuo. The residue was purified on a silica gel column and eluted with ethyl acetate/hexane to provide the title compound (1 mg).

$^1$H NMR (CDCl$_3$) 1.31-1.60 (6H, m), 1.4 (9H, s), 2.06 (1H, s), 2.43 (1H, m), 2.57 (2H, m), 3.13 (4H, m), 4.14 (1H, bs), 4.58 (1H, bs), 5.03 (1H, bs), 5.87 (2H, dd), 6.11 (1H, s), 6.68 (1H, t)

The t-BOC amino protecting group may be removed using a known deblocking reagent such as hydrochloric acid, trifluoroacetic acid, trimethylsilyl iodide, trimethysilyl chloride, trimethylsilyl triflate, and aluminum chloride, to give 1-hydroxy-8-[[(aminopentyl aminocarbonyl]oxy]-bicyclo[7.3.1]trideca-4,9-diene-2,6-diyne-13-one.

EXAMPLE 13

1,8-Dihydroxy-bicyclo[7.3.1]trideca-2,6-diyne-9,10-epoxy-4-ene-13-one

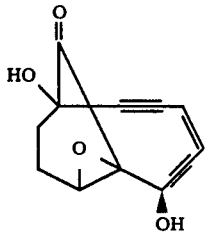

To a solution of the product of Example 2 (113.2 mg, 0.344 mmol) in 13 ml of methylene chloride was added 1.5 eq of triethylamine (75 ul, 0.516 mmol) and 1.2 eq of tert-butyl dimethylsilyl trifluoromethanesulfonate (95 ul, 0.413 nmmol). The reaction mixture was stirred at ambient temperature for 18 minutes, washed with water, and the aqueous layer extracted 2 times with methylene chloride. The organic layer was dried over sodium sulfate and concentrated in vacuo. The residue was purified by flash column chromatography on a silica gel column eluting with ethyl acetate/hexane to give the 1,8-bis(TBS)-protected starting material as a yellow solid in 94% yield (143.3 mg).

To a solution of this bis silyl compound (123.4 mg, 0.28 mmol) in 13 ml of methanol was added 600ul of 30% hydrogen peroxide and 300 ul of 6N sodium hydroxide. The reaction mixture was stirred at ambient temperature, and an additional 1 ml of 30% hydrogen peroxide and 375 ul of 6N sodium hydroxide was added portionwise over a 12 minute period. The reaction was quenched with saturated solution of ammonium chloride. The aqueous layer was extracted 3 times with methylene chloride and once with ether. The organic layer was washed with water, dried over sodium sulfate, and concentrated in vacuo to provide the 1,8-bis(TBS)-protected title compound (121.8 mg) in crude form.

Without further purification, the bis silyl epoxide was dissolved in 37 ml of methylene chloride. To this solution was added 2.5 g of 4A molecular sieves, and this mixture was stirred at ambient temperature for 10 minutes. Trifluoromethanesulfonic acid (40 ul, 20ul, 6 ul, -0.76 mmol) was added portionwise in 5 minute intervals. The reaction mixture was taken up in methylene chloride and washed with saturated solution of sodium bicarbonate. The aqueous layer was extracted 3 times with methylene chloride and once with ether. The organic layer was dried over sodium sulfate and concentrated in vacuo.

The residue from this reaction was combined with 10 mg. of the same from an earlier experiment and purified by flash column chromatography on a silica gel column using ether/pentane as eluant to give the title compound (59.4 mg, 79% overall yield).

IR (KBr): 3434, 2922, 2852, 2196, 1736, 1632, 1246, 1218, 1138, 914, 846

$^1$H NMR (CDCl$_3$): 1.89 (1H, m), 1.98 (1H, m), 2.32 (2H, m), 3.40 (1H, s), 3.74 (1H, s), 3.91 (1H, d), 4.31 (1H, d), 5.96 (2H, s)

$^{13}$C NMR (CDCl$_3$): δ 21.056, 25.844, 58.572, 68.515, 73.281, 76.736, 87.940, 93.218, 95.216, 97.393, 123.990, 124.726, 200.073

MS: 231 (M+), 213, 197, 185, 169, 157, 141, 129,

EXACT MASS: Calculated for C$_{13}$H$_{10}$O$_4$ 231.0657
Experimental Value 231.0653

EXAMPLE 14

1-Hydroxy-bicyclo[7.31]trideca-2,6-diyne-4-ene-13-one

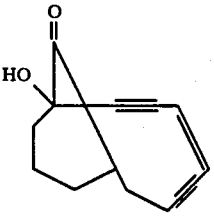

(a) (Z)-5-chloro-1-phenoxy-4-pentene-2-yne

To a 1 L flask under Argon was added CuI (7.86 g, 41.2 mmol) and Pd(PPh$_3$)$_4$ (5 g, 4.3 mmol). The catalyst was covered With 600 mL of degassed THF, cis-1,2-dichloroethylene (50 g, 516 mmol), and butylamine (68 mL, 688 mmol). Phenoxy-2-propyne (45g, 340 mmol) was added neat over 10 min and the reaction mixture stirred for 5.5 h. Air was bubbled through the reaction mixture for 15 min and the reaction filtered through a pad of celite and washed with pentane. The filtrate was washed with water and brine and the aqueous fractions extracted with ether. The organic fractions were combined, dried (MgSO$_4$), filtered through celite and concentrated. The residue was chromatographed over silica gel (hexane) to give 44.3 g of a yellow oil (67%).

IR (film) 1598, 1494, 1236, 1214, 1032, 754, 690 cm$^{-1}$;

$^1$H NMR (CDCl$_3$, 300 MHz) δ 7.47 (m, 2H), 6.99 (m, 3H), 6.42 (d, J=7.5 Hz, 1H), 5.90 (dt, J=7.5, 2.0 Hz, 1H), 4.88 (d, J=1.9 Hz, 2H).

$^{13}$C NMR (CDCl$_3$, 75.5 MHz) δ 157.5, 129.5, 129.4, 121.4, 114.9, 111.3, 92.1, 80.9, 56.3;

(b) (Z)-7-phenoxy-1-trimethylsilyl-3-heptene-1,5-diyne

To a 1 L flask under Argon was added CuI (5.24 g, 27 mmol) and Pd(PPh$_3$)$_4$ (4.9 g, 4 mmol) and the catalyst covered with 500 mL of degassed THF. To this solution was added the product of step (a) (42.7 g, 220 mmol) and degassed butylamine (44 mL, 440 mmol). To this solution was added trimethylsilyl acetylene (29 g, 290 mmol) and the reaction mixture was stirred for 7 h. Air was bubbled through the solution for 15 min and the reaction mixture filtered through celite and washed with pentane. The filtrate was washed several times with water and the aqueous fractions extracted with ether. The organic fractions were combined, dried (MgSO$_4$) and concentrated. The residue was chromatographed over silica gel (hexane) to give 35.1 g of a tan oil (62%).

IR (film) 2144, 1600, 1494, 1250, 1214, 844, 754;

$^1$H NMR (CDCl$_3$, 300 MHz) δ 7.30 (m, 2H), 7.00 (m, 3H), 5.87 (s, 2H), 4.89 (s, 2H), 0.21 (s, 9H);

$^{13}$C NMR (CDCl$_3$, 75.5 MHz) δ 157.7, 129.3, 121.3, 120.4, 119.6, 114.8, 103.4, 101.5, 91.8, 84.1, 56.4, −0.31;

(c)
(Z)-6-[[(1,1-dimethylethyl)dimethyl]silyloxy]-6(7-phenoxy-3-heptene-1,5-diynyl)-1-trimethylsilyloxycyclohexene To a solution of the product of step (b) (5.0 g, 19.7 mmol) in 20 mL THF was added 5 mL of water and LiOH-H$_2$O (5.6 g, 133 mmol). The solution was stirred for 4 h, diluted with ether and washed with water. The aqueous layer extracted with ether and then ethyl acetate. The organic fractions were combined, dried (MgSO<) and concentrated. The residue was chromatographed over silica (30:1 hexane/ethyl acetate) to give 3.37 g of (94%) of 7-phenoxy-3-heptene-1,5-diyne.

This diynene (3.37 g, 18.5 mmol) was dissolved in 60 mL of THF and cooled to −78 °C. To the cold solution was added LiHMDS (20 mL, 1.0M in THF, 20 mmol) and stirred 20 min. To this solution was added 2-TBSoxy-2-cyclohexeneone (3.8 g, 16.8 mmol) in 20 mL of THF. The reaction was immediately brought to 0 °C. and stirred for 30 min. Trimethylsilyl chloride was added at 0 °C. (3.1 mL, 24.4 mmol) and stirred for 30 min. The solution was diluted with pentane and washed with water, dried (MgSO$_4$), and concentrated. The residue was chromatographed over silica (200:1 hexane/ethyl acetate) to give 5.22 g of the desired product (65%) and 627 mg of recovered diynene.

$^1$H NMR (CDCl$_3$, 300 MHz) δ 7.30 (m, 2H), 6.98 (m, 3H), 5.84 (m, 2H), 4.85 (d, J=1.8 Hz, 2H), 4.81 (t, J=4.0 Hz, 1H), 2.02 (m, 4H), 1.68 (m, 2H), 0.89 (s, 9H), 0.22 (s, 12H), 0.19 (s, 3H);

(d)
(Z)-6-[[(1,1-dimethylethyl)dimethyl]silyloxy]-6(7-phenoxy-3-heptene-1,5-diynyl)
-1-trimethylsilyloxycyclohexene hexacarbonyl cobalt complex To a solution of octacarbonyl dicobalt (4.0 g, 11.7 mmol) in 70 mL of heptane was added the product of step (c) (5.2 g, 10.8 mmol) in 30 mL of heptane. The solution was stirred for 2.5 h, concentrated and the residue chromatographed over silica gel (98:2 hexane/chloroform) to give 5.88 g of the desired cobalt complex as the major product (71%) and 1.06 g of the minor cobalt complexed isomer (13%).

$^1$H NMR (CDCl$_3$, 300 MHz) δ 7.28 (m, 2H), 6.98 (m, 3H), 6.67 (d, J=10.6 Hz, 1H), 5.83 (d, J=10.6 Hz, 1H), 5.34 (s, 2H), 4.82 (t, J=4.0 Hz, 1H), 2.01 (m, 4H), 1.75 (m, 1H), 1.56 (m, 1H), 0.87 (s, 9H), 0.17 (s, 12H), 0.14 (s, 3H);

(e)
1-[[(1,1-dimethylethyl)dimethyl]silyloxy]-bicyclo[7.3.1]trideca-2,6-diyne-4-ene-13-one, hexacarbonyl cobalt complex To the major cobalt complexed product of step (d) (5.02 g, 6.54 mmol) in 265 mL of dichloromethane at −15 °C. was added ethyl aluminum dichloride (3.8 mL, 1.8 M in toluene, 6.84 mmol). The reaction mixture was stirred for 30 min and poured into water. The organic fraction was separated and the aqueous fraction washed with hexane. The organic fractions were combined, dried (MgSO$_4$), and concentrated. The residue was chromatographed over silica gel (30:1 hexane/ethyl acetate) to give 2.64 gm of a burgundy solid (67%).

$^1$H NMR (CDCl$_3$, 300 MHz) δ 6.97 (d, J=9.8 Hz, 1H), 5.73 (d, J=9.8 Hz, 1H), 4.22 (t, J=15.1 Hz, 1H), 3.18 (m, 2H), 2.39 (br d, J=13.0 Hz, 1H), 2.04 (m, 1H), 1.90

(f) 1-[[(1,1-dimethylethyl)dimethyl]silyloxy]-bicyclo 7.3.1]trideca-2,6-diyne-4-ene-13-one To the cyclized cobalt complex of step (e) (1.21 g, 2.0 mmol) was added 41 mL of 95% ethanol and ferric nitrate nonahydrate (4.05 g, 10.0 mmol) and the solution stirred for 3 h. Another equivalent of ferric nitrate was added (807 mg, 2.0 mmol) and the reaction stirred for an additional 2 h. The solution was diluted with ether and washed with water and brine. The organic fraction was dried (MgSO$_4$) and concentrated. The residue was chromatographed over silica gel (40:1 hexane/ethyl acetate) to give 541 mg of a white crystaline solid (86%).

$^1$H NMR (CDCl$_3$, 300 MHz) δ 5.85 (s, 2H), 3.20 (dd, J=17.5, 3.0 Hz, 1H), 2.71 (m, 2H), 2.40 (dd, J=17.5, 3.0 Hz, 1H), 2.36 (m, 1H), 2.00 (m, 2H), 1.73 (m, 2H), 0.90 (s, 9H), 0.19 (s, 3H), 0.17 (s, 3H);

(g)
1-Hydroxy-bicyclo[7.3.1]trideca-2,6-diyne-4-ene-13-one

A solution of 1.0M tetra-nbutyl ammonium fluoride in THF (0.3375 mL & mmol) was added to a solution of 96.5 mg (0.3375 mmol) of the product of step (f) stirring in 5 mL of THF at 25° under an N$_2$ atmosphere. After 30 min 50 mL of water was added and the mixture was extracted with three 25 mL portions of diethyl ether. The combined organic extracts were washed with saturated aqueous brine and dried over sodium sulfate. Flash chromatography (twice) over silica gel using 20% EtOAc/hexane provided 44 mg (72%) of the title compound as a white solid:

IR (NaCl) 3466, 2200, 1718, 1456, 1424 cm$^{-1}$.

$^1$H NMR (CDCl$_3$) δ 5.82 (s,2H), 4.04 (bs, —OH), 3.19 (dd, J=17.6,2.44Hz,1H), 2.85–2.70 (m,2H), 2.51–2.41 (m,2H), 2.05–1.85 (m,2H), 1.78–1.65 (m,2H).

$^{13}$C NMR (CDCl$_3$) δ 207.17, 125.33, 122.19, 99.98, 97.42, 90.32, 84.14, 72.11, 47.75, 33.73, 24.11, 24.02, 18.40.

Example 15

1-Hydroxy-bicylco[7.3.1]trideca-4,9-diene-2,6-diyne-13-one

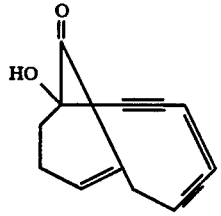

1-[[(1,1-dimethyethyl)dimethyl]silyloxy]bicyclo[7.3.1]trideca-4,9-diene-2,6-diyne-13-one To the product of Example 14 (593 mg, 1.88 mmol) in 40 mL of THF at −78 ° C. was added KHMDS (4.7 mL, 0.5M in toluene, 2.35 mmol) and stirred 20 min. 2,2′-Dipyridyl disulfide (515 mg, 2.34 mmol) in 2 mL of THF was added to the deeply colored enolate. The reaction was held at −78° C. for 30 min and then poured into water and diluted with ether. The organic fraction was dried (MgSO$_4$), concentrated and chromatographed over silica (20:1 hexane/ethyl acetate) to give 583 mg of 9-(2-pyridylthio)-substituted starting material (73%) which was immediately oxidized.

This sulfide (585 mg, 1.376 mmol) was dissolved in mL dichloromethane and cooled to 0 ° C. To the cold solution was added mCPBA (453 mg, 55%, 1.44 mmol) and the solution was stirred for 30 min. The cold bath was removed and the solution stirred at room temperature for h. The solution was diluted with chloroform and washed with sat. bicarbonate, dried (MgSO$_4$), and concentrated. The residue was chromatographed over silica gel (30:1 hexane/ethyl acetate) to give 412 mg of the desired product as a white solid (70%).

$^1$H NMR (CDCl$_3$, 300 MHz) δ 6.34 (br t, J=3.0 Hz, 1H), 5.81 (s, 2H), 3.66 (d, J=16.7 Hz, 1H), 2.99 (d, J=16.7 Hz, 1H), 2.48 (m, 2H), 2.29 (m, 1H), 2.14 (m, 1H), 0.92 (s, 9H), 0.21 (s, 3H), 0.17 (s, 3H);

(b)
1-Hydroxy-bicylco[7.3.1]trideca-4,9-diene-2,6-diyne-13-one

To the product of step (a) (73 mg, 0.234 mmol) was added 10.5 mL of acetonitrile and 1.8 mL of 48% HF and the solution was stirred in a plastic reactor for 18 h. The solution was diluted with chloroform and washed with water. The aqueous fraction was extracted with chloroform and the organic fractions combined, dried (K$_2$CO$_3$), and concentrated. The residue was chromatographed over silica gel (5:1 hexane/ethyl acetate) to give 44 mg of the title compound as a white solid (96%).

IR(KBr) 3468, 2186 (W), 1692, 1640, 1364, 1340, 1128, 1108, 1046, 964 cm$^{-1}$;

$^1$H NMR (CDCl$_3$, 300 MHz) δ 6.48 (m, 1H), 5.79 (s, 2H), 4.08 (s, 1H), 3.77 (d, J=16.7 Hz, 1H), 3.04 (d, J=16.7 Hz, 1H), 2.51 (m, 2H), 2.45 (m, 1H), 2.06 (m, 1H);

$^{13}$C NMR (CDCl$_3$, 75.5 MHz) δ 192.8, 141.2, 135.4, 24.4, 121.2, 99.9, 95.5, 90.6, 87.4, 72.0, 32.0, 24.8, 23.9;

MS (DCI) m/z 199 M$^+$, 181 M$^+$—OH), 153 (MH$^+$—CO);

EXAMPLE 16

1,11-Dihydroxy-bicyclo[7.3.1]trideca-4,9-diene-2,6-diyne-13-one

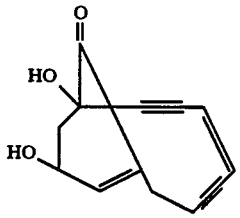

(a)
1-[[(1,1-dimethylethyl)dimethyl]silyloxy]-11-hydroxy-bicyclo-[7.3.1]trideca-4,9-diene-2,6-diyne-13-one and 1-[[(1,1-dimethylethyl)dimethyl]silyloxy]-bicyclo[7.3.1]-trideca-4,9-diene-2,6-diyne-11,13-dione To the product of Example I5, step (a) (142 mg, 0.45 mmol) in 25 mL dioxane was added selenium dioxide (164 mg, 1.47 mmol) and the solution heated to 90 ° C. for 5 h. The solution was diluted with chloroform and washed with bicarbonate. The aqueous fraction was extracted with chloroform and the organic fractions combined and dried (MgSO$_4$). The solution was concentrated and the residue chromatographed over silica gel (3:1 hexane/ethyl acetate) to give 82 mg of allylic alcohol (55%), 6 mg of dione (4%) and 20 mg of recovered starting enone (14%).

enone:

IR (film) 3424, 2956, 2930, 2856, 2194 (w), 1716, 1256, 1162, 1040, 1014, 976, 834, 782 cm$^{-1}$;

$^1$H NMR (CDCl$_3$, 300 MHz) δ 6.38 (t, J=2.5 Hz, 1H), 5.82 (ABq, 2H), 4.55 (m, 1H), 3.73 (d, J=16.6 Hz, 1H), 3.04 (d, J=16.6 Hz, 1H), 2.80 (ddd, J=12.9, 6.1, 20 Hz, 1H), 2.08 (dd, J=12.9, 9.6 Hz, 1H), 0.92 (s, 9H), 0.21 (s, 3H), 0.18 (s, 3H);

MS (DCI) m/z 329 (MH$^+$), 311(MH$^+$—OH), 271(MH$^+$—tBu), 197(MH$^+$—OSiMe$_2$tBu)

dione:

$^1$H NMR (CDCl$_3$, 300 MHz) δ 6.39 (s, 1H), 5.86 (s, 2H), 3.84 (d, J=16.1 Hz, 1H), 3.25 (dd, J=17.4, 1.7 Hz, 1H), 3.21 (d, J=16.1 Hz, 1H), 2.95 (d, J=17.4 Hz, 1H), 0.91 (s, 9H), 0.20 (s, 3H), 0.17 (s, 3H);

(b)
11,1-Dihydroxy-bicyclo[7.3.1]trideca-4,9-diene-2,6-diyne-13-one

To the protected allylic alcohol of step (a) (88 mg, 0.268 mmol) was added 8.5 mL of acetonitrile and 2.5 mL of 48% HF and the reaction stirred 30 h. The solution was diluted with chloroform and washed with water. The aqueous fraction was extracted with chloroform and the organic fractions combined and dried over K$_2$CO$_3$. The solution was concentrated and chromatographed over silica (1:1 hexane/ ethyl acetate) to give 58 mg of the title compound as a white solid (quantitative).

IR (KBr) 3388, 2188 (W), 1706, 1156, 1038 cm$^{-1}$;

$^1$H NMR (CDCl$_3$, 300 MHz) δ 6.50 (t, J=2.5 Hz, 1H), 5.80 (ABq, 2H), 4.60 (m, 1H), 4.04 (br s, 1H), 3.70 (d, J=16.6 Hz, 1H), 3.08 (d, J=16.6 Hz, 1H), 2.91 (d ABq, 1H), 2.02 (ABq, 1H);

$^{13}$C NMR (DMSO, 75.5 MHz) δ 194.1, 144.4, 136.5, 125.6, 122.6, 101.3, 97.6, 91.2, 88.9, 74.0, 67.2, 44.0, 24.9;

EXAMPLE 17

1-Hydroxy-bicyclo[7.3.1]trideca-4,9-diene-2.6-diyne-11,13-dione

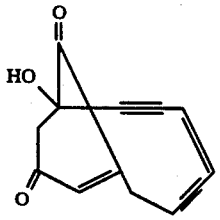

The silyl protected dione obtained in Example 16, step (a) was dissolved in 4.25 mL of acetonitrile and stirred with 0.75 mL of 48% HF for 24 h. The solution was diluted with chloroform and washed with water. The organic fraction was dried over $K_2CO_3$, concentrated and the residue chromatographed over silica gel (3:1 hexane/ethyl acetate) to yield 4.5 mg of the deprotec.ted dione (88%).

$^1$H NMR (CDCl$_3$, 300 MHz) δ 6.48 (s, 1H), 5.87 (s, 2H), 3.92 (s, 1H), 3.88 (d, J=16.3 Hz, 1H), 3.42 (d, J=17.6 Hz, 1H), 3.26 (d J=16.3 Hz, 1H), 2.94 (d, J=17.6 Hz, 1H);

EXAMPLE 18

1,8-Dihydroxy-bicyclo[7.3.1]trideca-4-ene-2,6-divne-13-one

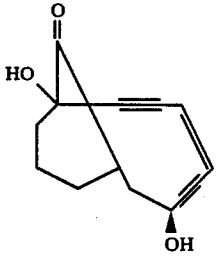

Bromine (0.341 mL) was added dropwise to a solution of 1.5 g (6.62 mmol) of 2-(t-butyldimethylsilyloxy)-2-cyclohexenone stirring in 100 mL of $CH_2Cl_2$ at 25° under an atmosphere of nitrogen. The color of the the bromine was nearly completely discharged after addition was complete. After 5 min 2.2 mL of triethylamine was added and the reaction was stirred for 2.5h. The reaction was poured into 50mL of water and extracted. The aqueous layer was reextracted with 10 mL of $CH_2Cl_2$ and the combined organic extracts were dried over anhydrous sodium sulfate. Concentration in vacuo provided a tan solid which was purified by flash chromatography over silica gel using 3-ethyl acetate in hexane as eluent. Concentration of the product fractions in vacuo provided 1.85 g (91%) of white crystalline solid which was the desired 3-bromo-2-TBSoxy-2-cyclohexenone. Spectroscopy showed this material to be about 95% pure and to contain about 5% of the starting enone.

A 1.0M solution of lithium bistrimethylsilylamide in tetrahydrofuran (5.7 mL) was added to a solution of 0.97 g (5.44 mmol) of (Z)-1-lithio-7,7-diethoxy-3-heptene-1,5-diyne in 54 mL of THF stirring at −78° . A solution of the bromide prepared as above (1.58 g, 5.18 mmol) in 10 mL of THF at −78° was added via cannula over 1 min. The cooling baths were removed and the reaction allowed to stir at ambient temperature (25° ) for 1.25h. The reaction was poured into 200 mL of water and extracted with 300 mL of 3:1 diethyl ether/ethyl acetate. The aqueous layer was reextracted with 100 mL of diethyl ether and then the combined organic extracts were washed with 100 mL of saturated brine. The extracts were dried over sodium sulfate, filtered, and concentrated in vacuo to provide 2.22 g of brown syrup which by $^1$H NMR was amixture of a major and minor bromoketone (Z)-2-bromo-6-TBSoxy-6-(7,7-diethoxy-3-heptene-1,5-diynyl)cyclohexanone. This crude material was used directly in the cobalt complexation step.

Octacarbonyl dicobalt (0.17 g) was added to a solution of 0.241 g of the bromoketones in 15 mL of $CH_2Cl_2$ stirring at 25° under an $N_2$ atmosphere. The reaction was stirred for 1h, concentrated in vacuo, and purified by flash chromatography. Isolation of only the major product provided 166 mg of a dark reddish purple oil which was a single compound and the desired cobalt complex of (Z)-2-bromo-6-TBSoxy-6-(7,7-diethoxy-3-heptene-1,5-diynyl)cyclohexanone.

Titanium tetrachloride (71 ul) was added in one portion to a solution of the above cobalt complexed (Z)2-bromo-6-TBSoxy-6-(7,7-diethoxy-3-heptene-1,5diynyl)-cyclohexanone (166 mg) and DABCO (25 mg) in 15 mL $CH_2Cl_2$ stirring at −78° under an atmosphere of nitrogen. The reaction was stirred for 5 minutes and then poured into water. The reaction was extracted and dried over sodium sulfate. Filtration, concentration, and purification by flash chromatography over silica gel using 5% ethyl acetate in hexane provided 121 mg of the desired cobalt complexed (Z)-2-bromo-6-TBSoxy-6-(7-oxo-3-heptene-1,5-diynyl)cyclohexanone as a purple oil.

Activated granular zinc (19 mg) was added to a solution of 0.21 mL 1.0M $Et_2AlCl$ in hexanes, 2.0 mL Ti-(OiPr)$_4$, 2 mg CuBr, and 0.121 g of cobalt complexed (Z)-2-bromo-6-TBSoxy-6-(7-oxo-3-heptene-1,5-diynyl)oyclohexanone stirring at 2° in 4.5mL of dry THF. The reaction was allowed to warm to 10° over 20 min and then was allowed to stir for 60 min during which time the temperature was maintained between 10° and 20° . The reaction was poured into 40 mL of 1N HCl and 50 mL diethyl ether and extracted. The aqueous layer was reextracted with an additional 10 mL of diethyl ether and the combined organic extracts were dried over sodium sulfate. Filtration, concentration in vacuo, and purification by flash chromatography on silica gel using 5% then 10% ethyl acetate in hexane as eluent provided 35 mg of reddish purple oil which was the desired cobalt complexed 8-hydroxy-1-TBSoxy-bicyclo[7.3.1]-trideca-4-ene-2,6-diyne-13-one.

Solid Fe(NO$_3$)$_3$.9H$_2$O (0.48g) was added in one portion to a solution of 0.24 g cobalt complexed 8-hydroxy-1-TBSoxy-bicyclo[7.3.1]trideca-4-ene-2,6-diyne-13-one stirring in 45mL of $CH_2Cl_2$ at 25° . The reaction was stirred for 3h and then an additional 155 mL of $CH_2Cl_2$ and 0.66 g ferric nitrate was added. The reaction was stirred for 40 min and then an additional 0.71 g of ferric nitrate was added. The reaction was stirred for 1h and then 200 mL of water was added. The reaction was extracted and the aqueous layer was rextracted with 200 mL of diethyl ether. The combined organic extracts were washed with saturated brine and then dried over sodium sulfate. Flash chromatography over silica gel using 3% then 5% ethyl acetate in hexane as eluent provided 72 mg of the desired 8-hydroxy-1-TBSoxy-bicyclo[7.3.1]trideca-4-ene-2,6-diyne-13-one as an offwhite solid.

Trifluoromethane sulfonic acid (16 ul) was added in one portion to a solution of 65 mg 8-hydroxy-1-TBSoxybicyclo[7.3.1]trideca-4-ene-2,6-diyne-13-one in 20 mL of CH$_2$Cl$_2$ stirring over 1 g of 2A molecular sieves at 25°. The reaction was stirred for 10 min and then poured into 10%aq NaHCO$_3$ and CH$_2$Cl$_2$. The mixture was extracted and the organic extracts were dried over sodium sulfate. Filtration, concentration, and purification by flash chromotography over silica gel using 1:1 diethyl ether/hexane as eluent provided 26 mg of the desired 1,8-dihydroxy-bioyclo[7.3.1]trideca-4-ene-2,6-diyne-13-one:

$^1$H NMR (CDCl$_3$) 5.90 (s, 2H), 4.57 (m,1H), 3.95 (m, 1H) 3.83 (s,1H), 2.98 (m, 1H), 2.45 (m, 2H), 2.20–1.60 (m, 4H).

Compound A

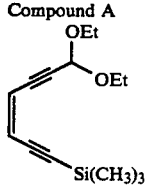

Compound B

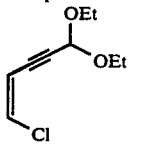

Compound C

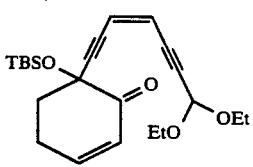

Compound D

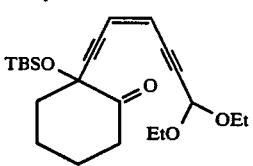

Compound E

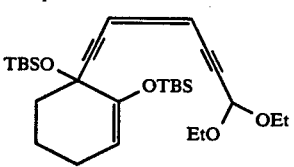

Compound F

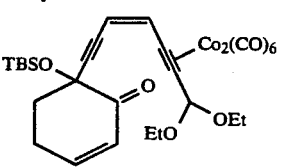

Compound G

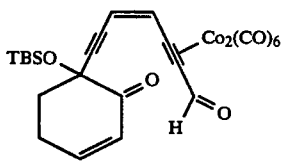

Compound H

Compound I

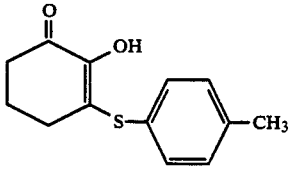

Compound J

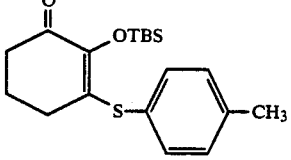

Compound K

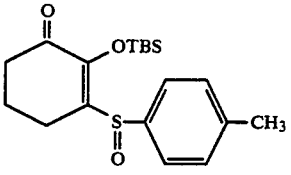

Compound L

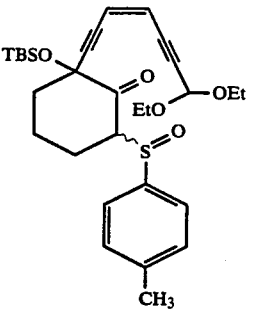

Compound M

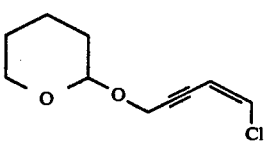

Compound N

53
-continued

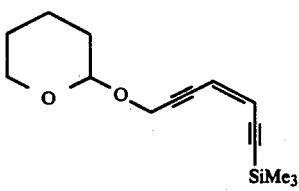
Compound O

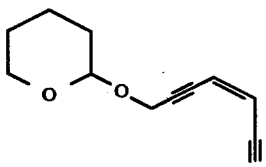
Compound P

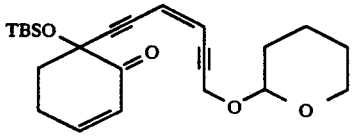
Compound Q

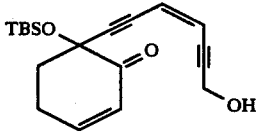
Compound R

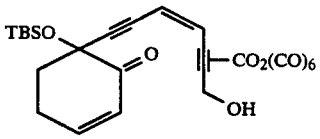
Compound S

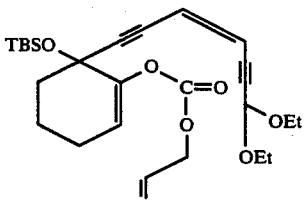

What is claimed is:

1. A compound having the formula

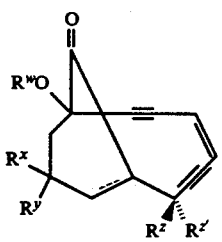

VIIa wherein

⁓ is a double bond, a single bond, or an epoxy;
    one of $R^x$ and $R^y$ is hydrogen and the other is hydrogen or hydroxy;

54

$R^w$ is hydrogen, —C(O)$R^s$, —C(O)NR$^t$R$^u$ or —C(O)OR$^v$;

$R^z$ and $R^{z'}$ are each hydrogen, or one of $R^z$ or $R^{z'}$ is hydrogen, and the other is hydroxy, —OC(O)R$^2$, —OC(O)NR$^t$R$^u$ or —OC(O)OR$^v$;

$R^s$ is hydrogen, $C_{1-8}$alkyl, $C_{3-6}$-cycloalkyl, $C_{6-10}$aryl, $C_{7-14}$aralkyl or quinoxalyl;

$R^t$ and $R^u$ are independently hydrogen, $C_{1-8}$alkyl, amino-substituted $C_{1-8}$alkyl, $C_{3-6}$-cycloalkyl, $C_{6-10}$aryl, $C_{7-14}$aralkyl, pyridyl or quinoxalyl; $R^v$ is $C_{1-8}$alkyl, halo-substituted $C_{1-8}$alkyl, $C_{3-6}$cycloalkyl, $C_{6-10}$aryl or $C_{7-14}$aralkyl; or a pharmaceutically acceptable salt thereof.

2. A compound of claim 1 having the formula

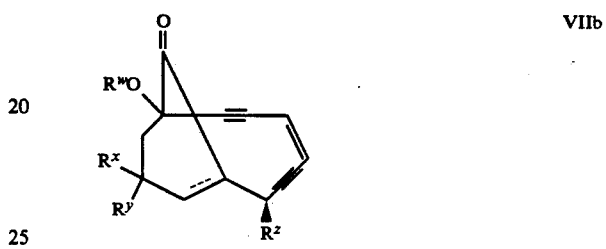

VIIb wherein

⁓ is a double bond, a single bond, or an epoxy;
    one of $R^x$ or $R^y$ is hydrogen and the other is hydrogen or hydroxy;
    $R^w$ is hydrogen, —C(O)R$^2$, —C(O)NR$^t$R$^u$ or —C(O)OR$^v$;
    $R^z$ is hydrogen, hydroxy, —OC(O)R$^s$, —OC(O)NR$^t$R$^u$ or —OC(O)OR$^v$;
    $R^s$ is hydrogen, $C_{1-8}$alkyl, $C_{3-6}$cycloalkyl, $C_{6-10}$aryl, $C_{7-14}$aralkyl or quinoxalyl;
    $R^t$ and $R^u$ are independently hydrogen, $C_{1-8}$alkyl, amino-substituted $C_{1-8}$alkyl, $C_{3-6}$cycloalkyl, $C_{6-10}$aryl, $C_{7-14}$aralkyl, pyridyl or quinoxalyl;
    $R^v$ is $C_{1-8}$alkyl, halo-substituted $C_{1-8}$alkyl, $C_{3-6}$cycloalkyl, $C_{6-10}$aryl or $C_{7-14}$aralkyl;
    or a pharmaceutically acceptable salt thereof.

3. A compound of claim 2 wherein $R^w$ is hydrogen.

4. A compound of claim 3 wherein $R^z$ is hydroxy, —OC(O)R$^2$, —OC(O)NR$^t$R$^u$ or —OC(O)OR$^v$; $R^s$, $R^t$, $R^u$ and $R^v$ are as defined in claim 14.

5. A compound of claim 4 wherein $R^x$ and $R^y$ are each hydrogen.

6. A compound of claim 5 wherein ⁓ is a double bond or an epoxy.

7. A compound of claim 6 wherein ⁓ is a double bond.

8. A compound of claim 7 wherein $R^z$ is hydroxy.

9. A compound of claim 7 wherein $R^z$ is —OC(O)R$^s$; $R^s$ is $C_{1-8}$alkyl or quinoxalyl.

10. A compound of claim 7 wherein $R^z$ is —OC(O)NR$^t$R$^u$; $R^t$ is hydrogen, and $R^u$ is $C_{1-8}$alkyl, amino-substituted $C_{1-8}$alkyl, pyridyl or quinoxalyl; or $R^t$ and $R^u$ are each $C_{1-8}$alkyl.

11. A compound of claim 7 wherein $R^z$ is —OC(O)OR$^v$; $R^v$ is halo-substituted $C_{1-8}$alkyl.

12. A compound of claim 9 wherein $R^s$ is methyl.

13. A compound of claim 9 wherein $R^s$ is quinoxalyl.

14. A compound of claim 10 wherein $R^t$ is hydrogen and $R^u$ is methyl.

15. A compound of claim 10 wherein $R^t$ is hydrogen and $R^u$ is quinoxalyl.

16. A compound of claim 10 wherein $R^t$ and $R^u$ are each ethyl.

17. A compound of claim 10 wherein $R^t$ is hydrogen and $R^u$ is 5-aminopentyl.

18. A compound of claim 10 wherein $R^t$ is hydrogen and $R^u$ is 2-pyridyl.

19. A compound of claim 11 wherein $R^v$ is 2,2,2-trichloroethyl.

20. A compound of claim 6 wherein $===$ is an epoxy.

21. A compound of claim 20 wherein $R^z$ is hydroxy.

22. A compound of claim 27 wherein $R^z$ is hydrogen.

23. A compound of claim 22 wherein $===$ is a single bond.

24. A compound of claim 23 wherein $R^x$ and $R^y$ are each hydrogen.

25. A compound of claim 22 wherein $===$ is a double bond.

26. A compound of claim 25 wherein $R^x$ and $R^y$ are each hydrogen.

27. A compound of claim 25 wherein one of $R^x$ or $R^y$ is hydroxy.

28. A method for treating malignant tumor sensitive to the compound of claim 1 in an animal which comprises administering to said animal an antitumor effective amount of a compound of claim 14.

29. A pharmaceutical composition comprising a compound of claim 1 and a pharmaceutically acceptable carrier.

* * * * *